United States Patent
Xu et al.

(10) Patent No.: US 10,865,444 B2
(45) Date of Patent: *Dec. 15, 2020

(54) AMPLICON PREPARATION AND SEQUENCING ON SOLID SUPPORTS

(71) Applicant: ILLUMINA, INC., San Diego, CA (US)

(72) Inventors: Hongxia Xu, San Francisco, CA (US); Alex Aravanis, San Mateo, CA (US); Shengrong Lin, Fremont, CA (US)

(73) Assignee: Illumina, Inc., San Diego, CA (US)

( * ) Notice: Subject to any disclaimer, the term of this patent is extended or adjusted under 35 U.S.C. 154(b) by 45 days.

This patent is subject to a terminal disclaimer.

(21) Appl. No.: 15/935,897

(22) Filed: Mar. 26, 2018

(65) Prior Publication Data

US 2018/0291444 A1 Oct. 11, 2018

Related U.S. Application Data

(63) Continuation of application No. 14/575,808, filed on Dec. 18, 2014, now Pat. No. 9,926,598.

(60) Provisional application No. 61/928,368, filed on Jan. 16, 2014.

(51) Int. Cl.
| | | |
|---|---|---|
| *C12Q 1/6837* | (2018.01) | |
| *C12Q 1/6874* | (2018.01) | |
| *C12N 15/10* | (2006.01) | |
| *C12Q 1/6806* | (2018.01) | |

(52) U.S. Cl.
CPC ....... *C12Q 1/6874* (2013.01); *C12N 15/1093* (2013.01); *C12Q 1/6806* (2013.01); *C12Q 1/6837* (2013.01)

(58) Field of Classification Search
CPC ............ C12Q 1/6874; C12Q 2525/161; C12Q 2565/501; C12Q 2565/514; C12Q 2565/518; C12Q 2565/543
See application file for complete search history.

(56) References Cited

U.S. PATENT DOCUMENTS

| | | | |
|---|---|---|---|
| 5,130,238 A | 7/1992 | Malek et al. | |
| 5,185,243 A | 2/1993 | Ullman et al. | |
| 5,455,166 A | 10/1995 | Walker | |
| 5,573,907 A | 11/1996 | Carrino et al. | |
| 5,679,524 A | 10/1997 | Nikiforov et al. | |
| 6,210,891 B1 | 4/2001 | Nyren et al. | |
| 6,214,587 B1 | 4/2001 | Dattagupta et al. | |
| 6,258,568 B1 | 7/2001 | Nyren | |
| 6,274,320 B1 | 8/2001 | Rothberg et al. | |
| 6,355,431 B1 | 3/2002 | Chee et al. | |
| 6,890,741 B2 | 5/2005 | Fan et al. | |
| 6,913,884 B2 | 7/2005 | Stuelpnagel et al. | |
| 7,001,792 B2 | 2/2006 | Sauer et al. | |
| 7,057,026 B2 | 6/2006 | Barnes et al. | |
| 7,115,400 B1 | 10/2006 | Adessi et al. | |
| 7,211,414 B2 | 5/2007 | Hardin et al. | |
| 7,244,559 B2 | 7/2007 | Rothberg et al. | |
| 7,315,019 B2 | 1/2008 | Turner et al. | |
| 7,329,492 B2 | 2/2008 | Hardin et al. | |
| 7,405,281 B2 | 7/2008 | Xu et al. | |
| 7,582,420 B2 | 9/2009 | Oliphant et al. | |
| 7,595,883 B1 | 9/2009 | El Gamal et al. | |
| 7,611,869 B2 | 11/2009 | Fan | |
| 7,670,810 B2 | 3/2010 | Gunderson et al. | |
| 8,003,354 B2 | 8/2011 | Shen et al. | |
| 8,728,764 B2 | 5/2014 | Boutell | |
| 9,926,598 B2 * | 3/2018 | Xu | C12Q 1/6874 |
| 2005/0053980 A1 | 3/2005 | Gunderson et al. | |
| 2005/0100900 A1 | 5/2005 | Kawashima et al. | |
| 2005/0181440 A1 | 8/2005 | Chee et al. | |
| 2005/0191698 A1 | 9/2005 | Chee et al. | |
| 2008/0108082 A1 | 5/2008 | Rank et al. | |
| 2009/0026082 A1 | 1/2009 | Rothberg et al. | |
| 2009/0118128 A1 | 5/2009 | Liu et al. | |
| 2009/0127589 A1 | 5/2009 | Rothberg et al. | |
| 2009/0186349 A1 | 7/2009 | Gunderson et al. | |
| 2010/0137143 A1 | 6/2010 | Rothberg et al. | |
| 2010/0282617 A1 | 11/2010 | Rothberg et al. | |
| 2011/0045541 A1 | 2/2011 | Kawashima et al. | |
| 2012/0122737 A1 | 5/2012 | Sabot et al. | |
| 2012/0157322 A1 | 6/2012 | Myllykangas et al. | |
| 2012/0316086 A1 | 12/2012 | Lin et al. | |
| 2013/0296176 A1 | 11/2013 | Marziali | |
| 2014/0249038 A1 | 9/2014 | Chen et al. | |
| 2015/0197798 A1 | 7/2015 | Xu | |

FOREIGN PATENT DOCUMENTS

| | | |
|---|---|---|
| CN | 102329876 | 1/2012 |
| CN | 102787118 | 11/2012 |
| CN | 103119179 | 5/2013 |
| EP | 0320308 B1 | 11/1993 |
| EP | 0336731 B1 | 5/1994 |

(Continued)

OTHER PUBLICATIONS

"International Search Report and Written Opinion for Application No. PCT/US2014/071263", dated Apr. 29, 2015.
Myllykangas, et al., "Efficient targeted resequencing of human germline and cancer genomes by oligonucleotide-selective sequencing", Nature Biotechnology, vol. 29, No. 11, Nov. 2011, 1024-1029.
Bentley et al., Accurate whole genome sequencing using reversible terminator chemistry, Nature 456: 53-59 (2008).
Cockroft et al. A single-molecule nanopore device detects SNA polymerase activity with single-nucleotide resolution, J. Am. Chem. Soc. 130, 818-820 (2008).

(Continued)

*Primary Examiner* — David C Thomas
(74) *Attorney, Agent, or Firm* — Knobbe Martens Olson & Bear LLP

(57) ABSTRACT

The present disclosure relates to the field of molecular biology and more specifically to methods for capturing, amplifying and sequencing target polynucleotides on a solid surface.

19 Claims, 8 Drawing Sheets

Specification includes a Sequence Listing.

(56) References Cited

FOREIGN PATENT DOCUMENTS

| | | |
|---|---|---|
| EP | 0439182 B1 | 4/1996 |
| JP | 2002-503954 | 2/2002 |
| JP | 2013-544498 | 12/2013 |
| JP | 2013-529471 A | 5/2016 |
| KR | 2013/0113447 A | 10/2013 |
| WO | WO 89/09835 | 10/1989 |
| WO | WO 89/12696 | 12/1989 |
| WO | WO 90/01069 | 2/1990 |
| WO | WO 91/06678 | 5/1991 |
| WO | 1998/44151 | 10/1998 |
| WO | WO 00/18957 | 4/2000 |
| WO | WO 04/018497 | 3/2004 |
| WO | WO 07/010251 | 1/2007 |
| WO | WO 07/123744 | 11/2007 |
| WO | WO 08/070675 | 6/2008 |
| WO | WO 11/057111 A2 | 5/2011 |
| WO | 2012/040387 A1 | 3/2012 |
| WO | WO 12/134884 | 10/2012 |
| WO | WO 13/130674 | 9/2013 |
| WO | 2013/166444 | 11/2013 |

OTHER PUBLICATIONS

Deamer et al., Characterization of nucleic acids by nanopore analysis, Acc. Chem. Res. 35: 817-825 (2002).

Deamer et al. Nanopores and nucleic acids: prospects for ultrarapid sequencing Trends Biotechnol. 18, 147-151 (2000).

Dean et al., Comprehensive human genome amplification using multiple displacement amplification Proc. Natl. Acad. Sci USA 99: 5261-66 (2002).

Emanuel and Pestka Amplification of specific products from human serum, GATA 10(6): 144-146 (1993).

Grothues et al. PCR amplification of megabase DNA with tagged random primers (T-PCR), Nucleic Acids Res. 21(5): 1321-2 (1993).

Healy, Nanopore-based single-molecule DNA analysis, Nanomed. 2, 459-481 (2007).

Korlach et al. Selective aluminum passivation for targeted immobilization of single DNA polymerase molecules in zero-mode waveguide nanostructures, Proc. Natl. Acad. Sci USA 105, 1176-1181 (2008).

Lage et al., Whole genome analysis of genetic alterations in small DNA samples using hyperbranched strand displacement amplification and array-CGH, Genome Research 13: 294-307 (2003).

Levene et al., Zero-mode waveguides for single-molecule analysis at high concentrations, Science 299, 682-686 (2003.

Li et al. DNA molecules and configurations in a solid-state nanopore microscope, Nat. Mater. 2: 611-615 (2003).

Lizardi et al., Mutation detection and single-molecule counting using isothermal rolling-circle amplification, Nat. Genet. 19: 225-232 (1998).

Lundquist et al. Parallel confocal detection of single molecules in real time, Opt. Lett. 33, 1026-1028 (2008).

Mulcahy et al., Cancer and Mutant DNA in Blood Plasma, Lancet 348: 628 (1996).

Ronaghi et al. A sequencing method based on real-time pyrophosphate, Science 281 (5375), 363 (1998).

Ronaghi, et al., Real-time DNA sequencing using detection of pyrophosphate release, Analytical Biochemistry 242(1), 84-9 (1996).

Ronaghi, Pyrosequencing sheds light on DNA sequencing, Genome Res. 11(1), 3-11 (2001).

Shapiro, Determination of Circulating DNA Levels in Patients with Benign or Malignant Gastrointestinal Disease, Cancer 51(11): 2116-20 (1993).

Soni et al. Progress toward ultrafast DNA sequencing using solid-state nanopores, Clin Chem. 53, 1996-2001 (2007).

Walker et al., Molecular Methods for Virus Detection, Academic Press, Inc., 1995.

Walker et al., Strand displacement amplification—an isothermal, in vitro DNA amplification technique, Nucl. Acids Res. 20: 1691-96 (1992).

\* cited by examiner

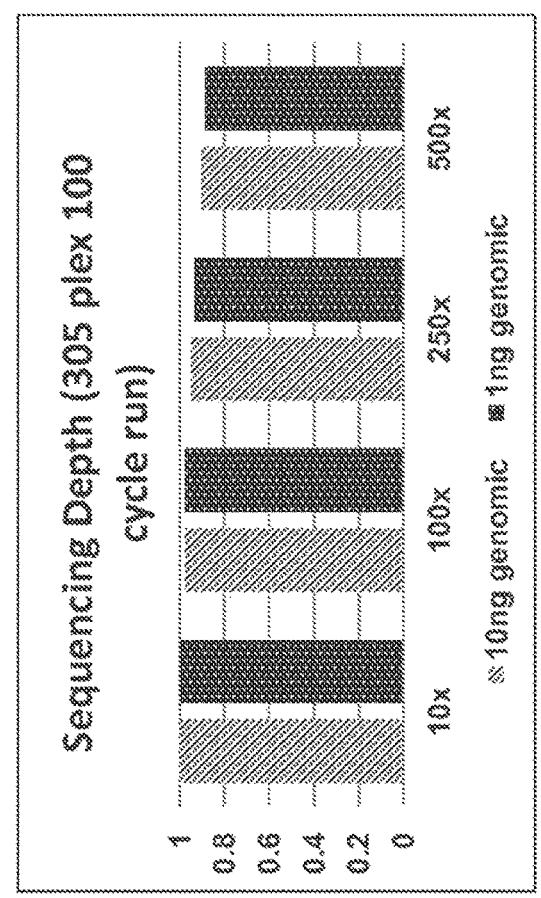
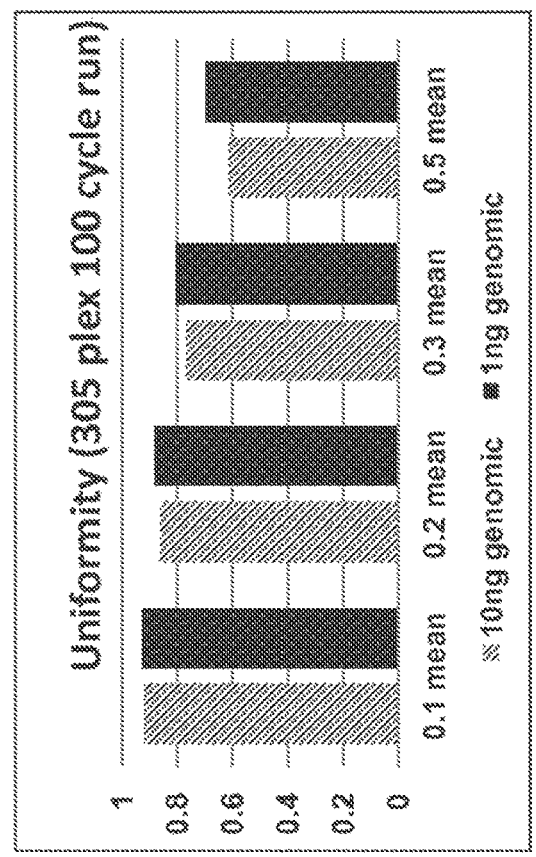
Figure 2

Figure 3
Performance of Human 305 plex on FFPE DNA*
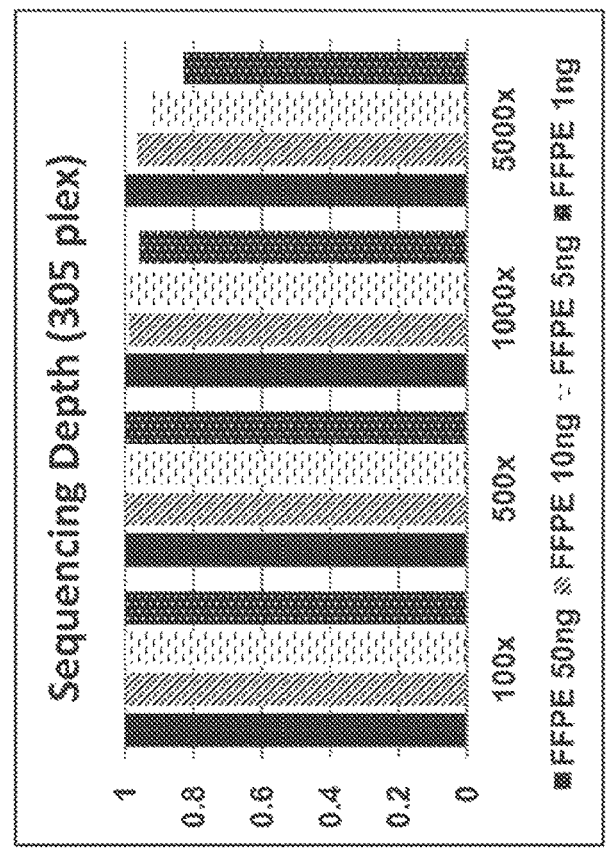
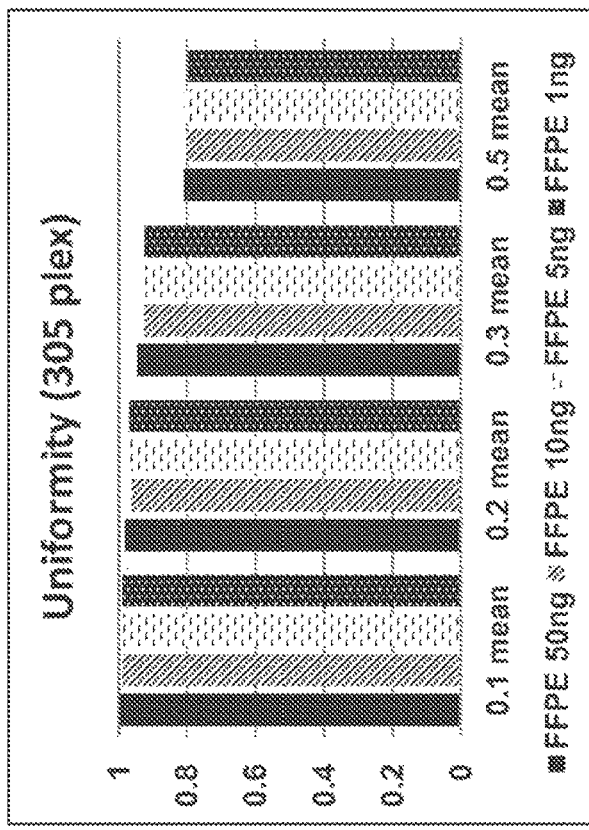
*Representation from two or more experiments.
*PF cluster ranges from 300-800k/mm²
*Specificity is more than 90%
*Based on 50 cycle run.

AMPLICON PREPARATION AND SEQUENCING ON SOLID SUPPORTS

CROSS-REFERENCE TO RELATED APPLICATIONS

This application is a continuation of U.S. application Ser. No. 14/575,808, filed Dec. 18, 2014, now U.S. Pat. No. 9,926,598, issued Mar. 27, 2018 which claims the benefit of U.S. Provisional Application No. 61/928,368, filed Jan. 16, 2014, the content of all of which is incorporated by reference in their entireties.

BACKGROUND

The present disclosure relates generally to methods and compositions for nucleic acid amplification and sequencing and, more specifically to capture and sequencing of target polynucleotides on a solid support.

As the information encoded in a polynucleotide (e.g., DNA or RNA) is of paramount importance to medicine and life science, there exists a need to sequence a polynucleotide rapidly and inexpensively. At present, commercial sequencing techniques require sample and library preparation, both of which are laborious. Furthermore, readouts are slower than desired for many applications. Therefore, throughput is limited and cost is relatively high.

Thus, there exists a need for more rapid and efficient methods for preparing and sequencing target polynucleotides. The present disclosure satisfies this need and provides related advantages as well.

SUMMARY OF EMBODIMENTS

The disclosure provides a method for amplicon preparation. The method includes: (a) contacting a nucleic acid sample including a plurality of target polynucleotides with at least one primer under conditions sufficient for hybridization, the at least one primer containing an adapter; (b) amplifying by polymerase chain reaction (PCR) the plurality of target polynucleotides to produce a plurality of amplicons; (c) directly contacting a plurality of target specific capture primers immobilized on a solid support with the plurality of amplicons under conditions sufficient for hybridization to produce a first plurality of immobilized amplicons, the solid support further including a plurality of universal capture primers; (d) extending the plurality of target specific capture primers to produce a plurality of immobilized extension products complementary to the target polynucleotides; (e) annealing the plurality of universal capture primers to the plurality of the immobilized extension products, and (f) amplifying by PCR the plurality of immobilized extension products to produce a second plurality of immobilized amplicons, wherein the population of immobilized amplicons includes a uniformity of 85% or more. The method can be used with 10 ng or less input nucleic acid and can further include sequencing the second plurality of immobilized amplicons. The method also can be used for determining the presence of a gene associated with a disorder or disease, including a cancer associated gene. Cell free DNA also can be employed in the method of the disclosure.

The disclosure further provides a method for increasing detection sensitivity of a nucleic acid sequence variant. The method includes: (a) contacting a nucleic acid sample including a plurality of target polynucleotides with gene specific forward and reverse primers under conditions sufficient for hybridization, each species of the gene specific forward primer including a unique sequence index and an adapter; (b) amplifying by polymerase chain reaction (PCR) the plurality of target polynucleotides to produce a plurality of amplicons; (c) directly contacting a plurality of target specific capture primers immobilized on a solid support with the plurality of amplicons under conditions sufficient for hybridization to produce a first plurality of immobilized amplicons, the solid support further including a plurality of universal capture primers; (d) extending the plurality of target specific capture primers to produce a plurality of immobilized extension products complementary to the target polynucleotides; (e) annealing the plurality of universal capture primers to the plurality of the immobilized extension products; (f) amplifying by PCR the plurality of immobilized extension products to produce a second plurality of immobilized amplicons, wherein the second plurality of immobilized amplicons includes a uniformity of 85% or more; (g) sequencing the second plurality of immobilized amplicons, and (h) eliminating random sequence errors for one or more target polynucleotide by comparing three or more nucleotide sequences at a variant position for a target polynucleotide species, wherein the target polynucleotide species are identified by the unique sequence index to thereby determine a true nucleotide sequence variant in the one or more target polynucleotides. The method can detect a mismatch rate of 0.3% or less for a variant nucleotide position.

BRIEF DESCRIPTION OF THE DRAWINGS

FIG. 2 shows a comparison of the sequencing uniformity and the sequencing depth for two different input amounts of nucleic acid for a multiplex 100 cycle sequencing run of genomic DNA.

FIG. 3 shows a comparison of the sequencing uniformity and the sequencing depth for four different input amounts of nucleic acid for a multiplex 50 cycle sequencing run of DNA obtained from formalin-fixed, paraffin embedded tissue.

DETAILED DESCRIPTION OF EMBODIMENTS

Figure 1:
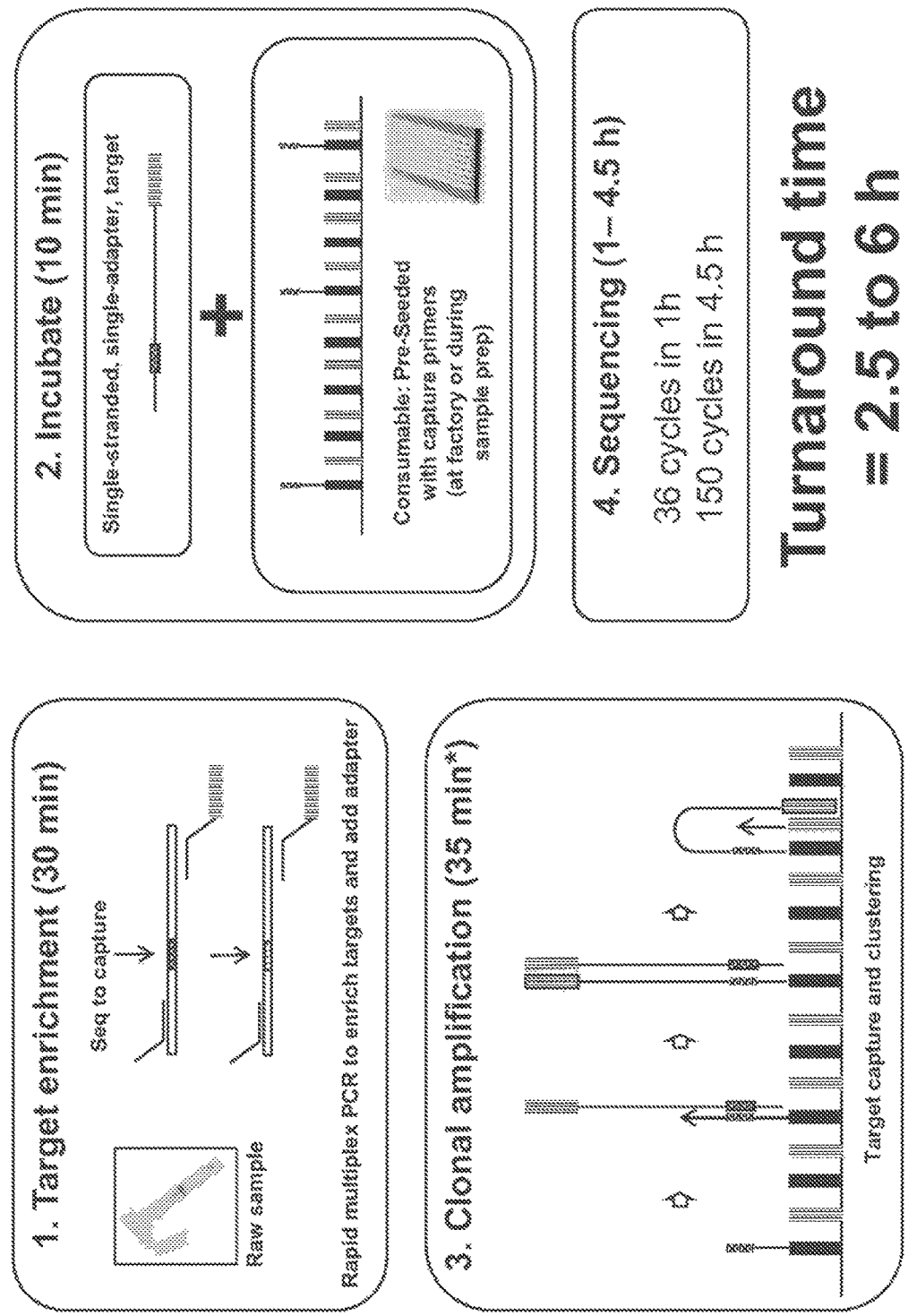
FIG. 1 is a schematic showing exemplary steps in the preparation and sequencing of amplicons on a solid support.

This disclosure is directed to methods for the rapid and efficient preparation and sequencing of target polynucleotides. The methods include polymerase chain reaction (PCR) amplification of target polynucleotides, direct immobilization to a solid support, clonal amplification and sequencing. They can be employed individually or utilized together in an integrated procedure that allows rapid sample-to-answer amplicon sequencing. The integrated method is particularly useful because amplicon library preparation is unnecessary, thereby eliminating inefficiencies related to ligation. Other particularly useful attributes of the integrated method for sequencing include, for example, eliminating the need for amplicon purification and additional enrichment steps following PCR, allows for rapid hybridization step for amplicon immobilization, and can be utilized with very small amounts of input nucleic acid while achieving high quality sequencing results.

In one specific embodiment, the methods of the disclosure employ multiplex PCR of a population of target polynucleotides where one primer contains an adapter that is complimentary to an oligonucleotide immobilized on a solid support. The amplified population of target polynucleotides are immobilized onto a solid support without first being subjected to a purification step. Immobilization is by hybridization to target specific capture oligonucleotides that have been pre-seeded onto the solid support. The adapter end of the amplified population of target polynucleotides are annealed to the immobilized complimentary oligonucleotides and the complimentary oligonucleotides are used as a primer in an extension reaction to yield produce a population of double strand target polynucleotides. Following clonal amplification the target polynucleotide colonies are subjected to multiplex sequencing consisting of 35 cycles or more.

As used herein, the term "plurality" refers to a population of two or more different polynucleotides or other referenced molecule. Accordingly, unless expressly stated otherwise, the term "plurality" is used synonymously with population. A plurality includes 2, 3, 4, 5, 6, 7, 8, 9, 10, 20, 30, 40, 50, 60, 70, 80, 90 or a 100 or more different members of the population. A plurality also can include 200, 300, 400, 500, 1000, 5000, 10000, 50000, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$ or $1\times10^7$, or more different members. A plurality includes all integer numbers in between the above exemplary population numbers.

As used herein, the term "target polynucleotide" is intended to mean a polynucleotide that is the object of an analysis or action. The analysis or action includes subjecting the polynucleotide to copying, amplification, sequencing and/or other procedure for nucleic acid interrogation. A target polynucleotide can include nucleotide sequences additional to the target sequence to be analyzed. For example, a target polynucleotide can include one or more adapters, including an adapter that functions as a primer binding site, that flank(s) a target polynucleotide sequence that is to be analyzed. A target polynucleotide hybridized to a capture oligonucleotide or capture primer can contain nucleotides that extend beyond the 5' or 3' end of the capture oligonucleotide in such a way that not all of the target polynucleotide is amenable to extension. In particular embodiments, as set forth in further detail below, a plurality of target polynucleotides includes different species that differ in their target polynucleotide sequences but have adapters that are the same for two or more of the different species. The two adapters that can flank a particular target polynucleotide sequence can have the same sequence or the two adapters can have different sequences. Accordingly, a plurality of different target polynucleotides can have the same adapter sequence or two different adapter sequences at each end of the target polynucleotide sequence. Thus, species in a plurality of target polynucleotides can include regions of known sequence that flank regions of unknown sequence that are to be evaluated by, for example, sequencing. In cases where the target polynucleotides carry an adapter at a single end, the adapter can be located at either the 3' end or the 5' end the target polynucleotide. Target polynucleotides can be used without any adapter, in which case a primer binding sequence can come directly from a sequence found in the target polynucleotide.

As used herein, the term "directly" when used in reference to contacting a plurality of capture primers is intended to mean that the contacting material is applied to the plurality of capture primers without a significant intervening purification step following a referenced procedure. Significant intervening purification steps include those procedures that are intended to reduce the complexity of cellular components, including reducing the presence of primers, enzymes and unamplified or incorrectly amplified templates following an amplification reaction, for example. Significant intervening purification steps is not intended to include modification of buffers, precipitation of the sample nucleic acids and other minor nucleic acid manipulation procedures.

As used herein, the term "capture primers" is intended to mean an oligonucleotide having a nucleotide sequence that is capable of specifically annealing to a single stranded polynucleotide sequence to be analyzed or subjected to a nucleic acid interrogation under conditions encountered in a primer annealing step of, for example, an amplification or sequencing reaction. Generally, the terms "nucleic acid," "polynucleotide" and "oligonucleotide" are used interchangeably herein. The different terms are not intended to denote any particular difference in size, sequence, or other property unless specifically indicated otherwise. For clarity of description the terms can be used to distinguish one species of nucleic acid from another when describing a particular method or composition that includes several nucleic acid species.

As used herein, the term "target specific" when used in reference to a capture primer or other oligonucleotide is intended to mean a capture primer or other oligonucleotide that includes a nucleotide sequence specific to a target polynucleotide sequence, namely a sequence of nucleotides capable of selectively annealing to an identifying region of a target polynucleotide. Target specific capture primers can have a single species of oligonucleotide, or it can include two or more species with different sequences. Thus, the target specific capture primers can be two or more sequences, including 3, 4, 5, 6, 7, 8, 9 or 10 or more different sequences. The target specific capture oligonucleotides can include a target specific capture primer sequence and universal capture primer sequence. Other sequences such as sequencing primer sequences and the like also can be included in a target specific capture primer.

In comparison, the term "universal" when used in reference to a capture primer or other oligonucleotide sequence is intended to mean a capture primer or other oligonucleotide having a common nucleotide sequence among a plurality of capture primers. A common sequence can be, for example, a sequence complementary to the same adapter sequence. Universal capture primers are applicable for interrogating a plurality of different polynucleotides without necessarily distinguishing the different species whereas target specific capture primers are applicable for distinguishing the different species.

As used herein, the term "index" when used in reference to a nucleotide sequence is intended to mean a unique nucleotide sequence that is distinguishable from other indices as well as from other nucleotide sequences within polynucleotides contained within a sample. A nucleotide index can be a random or a specifically designed nucleotide sequence. An index can be of any desired sequence length so long as it is of sufficient length to be unique nucleotide sequence within a plurality of indices in a population and/or within a plurality of polynucleotides that are being analyzed or interrogated. A nucleotide index of the disclosure is useful, for example, to be attached to a target polynucleotide to tag or mark a particular species for identifying all members of the tagged species within a population. Accordingly, an index is useful as a barcode where different members of the same molecular species can contain the same index and where different species within a population of different polynucleotides can have different indices.

As used herein, the term "immobilized" when used in reference to a nucleic acid is intended to mean direct or indirect attachment to a solid support via covalent or non-covalent bond(s). In certain embodiments of the disclosure, covalent attachment can be used, but generally all that is required is that the nucleic acids remain stationary or attached to a support under conditions in which it is intended to use the support, for example, in applications requiring nucleic acid amplification and/or sequencing. Typically, oligonucleotides to be used as capture primers or amplification primers are immobilized such that a 3' end is available for enzymatic extension and at least a portion of the sequence is capable of hybridizing to a complementary sequence. Immobilization can occur via hybridization to a surface attached oligonucleotide, in which case the immobilised oligonucleotide or polynucleotide can be in the 3'-5' orientation. Alternatively, immobilization can occur by means other than base-pairing hybridization, such as the covalent attachment set forth above.

As used herein, the term "solid support" is intended to mean any insoluble substrate or matrix to which nucleic acids can be attached, such as for example, latex beads, dextran beads, polystyrene surfaces, polypropylene surfaces, polyacrylamide gel, gold surfaces, glass surfaces and silicon wafers. The surface can be any desirable shape including, for example, planar, spherical or porous suitable for a particular application. For example, the solid support can be a planar glass surface. The solid support also can be mounted on the interior of a flow cell to allow the interaction with solutions of various reagents.

In certain embodiments the solid support can comprise an inert substrate or matrix which has been chemically functionalized, for example, by the application of a layer or coating of an intermediate material having reactive groups that permit covalent attachment to polynucleotides. The intermediate material can be directly or indirectly attached to the solid support via covalent or non-covalent bonds. By way of non-limiting example for non-covalent attachment to a solid support, such supports can include polyacrylamide hydrogel layers on an inert substrate such as glass. In such embodiments the polynucleotides can be covalently attached directly to the intermediate layer (for example, a hydrogel) but the intermediate layer can itself be non-covalently attached to other layers of the substrate or matrix (for example, a glass substrate).

The disclosure provides a method for amplicon preparation. The method includes: (a) contacting a nucleic acid sample having a plurality of target polynucleotides with at least one primer under conditions sufficient for hybridization, the at least one primer containing an adapter; (b) amplifying by polymerase chain reaction (PCR) the plurality of target polynucleotides to produce a plurality of amplicons; (c) directly contacting a plurality of target specific capture primers immobilized on a solid support with the plurality of amplicons under conditions sufficient for hybridization to produce a first plurality of immobilized amplicons, the solid support further having a plurality of universal capture primers; (d) extending the plurality of target specific capture primers to produce a plurality of immobilized extension products complementary to the target polynucleotides; (e) annealing the plurality of universal capture primers to the plurality of the immobilized extension products, and (f) amplifying by PCR the plurality of immobilized extension products to produce a second plurality of immobilized amplicons, wherein said second plurality of immobilized amplicons comprises a uniformity of 85% or more.

The method of amplicon preparation of the disclosure integrates one or more features that increases the sample quality of the target polynucleotide or interrogation product thereof to enable a rapid and efficient multi-step process for the preparation of clonal populations of immobilized target polynucleotides. Each preparation procedure results in a ready-to-use plurality of target polynucleotides that can be employed in any of the procedures described herein.

A method of the disclosure for amplicon preparation includes contacting a nucleic acid sample having a plurality of target polynucleotides with at least one primer under conditions sufficient for hybridization. The at least one primer can contain an adapter.

A nucleic acid sample can originate from any desired source including eukaryotic or prokaryotic sources as well as synthetic sources. In certain embodiments, the nucleic acid sample source will originate from a organism of interest and include genomic deoxyribonucleic acid (DNA). For example, the sample can originate from a human source where genetic information is desirable for diagnostic or therapeutic purposes. Similarly, the sample can originate from domestic or farm animal sources where genetic information also is desirable for diagnostic or therapeutic purposes. Other sources for a nucleic acid sample include, for example, bacteria, yeast, fungi, rodents and the like. Given the teachings and guidance provided herein, those skilled in the art will understand that any source of nucleic acid can be used in the methods of the disclosure.

A target polynucleotide includes any desired nucleic acid to be interrogated. In this regard, a target polynucleotide includes, for example, genomic DNA, cDNA, cell free DNA (cfDNA), ESTs, mRNA, hnRNA, rRNA, tRNA, snRNA, mitochondrial DNA and synthetic DNA or RNA. In particular embodiments, the target polynucleotides are genomic DNA and the interrogation is applicable for diagnostic information or therapeutic intervention.

Accordingly, the term "polynucleotide" refers to deoxyribonucleic acid (DNA) and ribonucleic acid (RNA). The term should be understood to include, as equivalents, analogs of either DNA or RNA made from nucleotide analogs and to be applicable to single stranded (such as sense or antisense) and double stranded polynucleotides.

The target polynucleotide molecules can originate in double-stranded DNA (dsDNA) form (e.g. genomic DNA fragments, PCR and amplification products and the like) or can have originated in single-stranded form, as DNA or RNA, and been converted to dsDNA form. By way of example, mRNA molecules can be copied into double-stranded cDNAs suitable for use in the method of the disclosure using standard techniques well known in the art. The precise sequence of the target polynucleotide molecules can be known or unknown.

The nucleic acid sample can be an initial sample of unenriched genomic DNA. As an example of genomic DNA useful as a nucleic acid sample, a human genome consists of approximately 3.1 billion bases of sequence. Exemplary size estimates for other genomes that can be used in the methods of the disclosure are about 2.7 Gbp (mouse), 2.8 Gbp (rat), 1.7 Gbp (zebrafish), 165 Mbp (fruitfly), 13.5 Mbp (*S. cerevisiae*), 390 Mbp (fugu), 278 Mbp (mosquito) or 103 Mbp (*C. elegans*). Those skilled in the art will recognize that genomes having sizes other than those exemplified above including, for example, smaller or larger genomes, can be used in a method of the disclosure.

In a particular embodiment, the target polynucleotide molecules are DNA molecules. More particularly, the target polynucleotide molecules represent the entire genetic complement of an organism, and are genomic DNA molecules which include both intron and exon sequences (coding sequence), as well as non-coding regulatory sequences such as promoter and enhancer sequences. Particular subsets of polynucleotide sequences or genomic DNA can also be used, such as particular chromosomes. Yet more particularly, the sequence of the target polynucleotide molecules or a portion thereof can be a target sequence. Still yet more particularly, the target polynucleotide molecules are genomic DNA molecules, for example, from human, mammalian, bacterial, fungal or plant genomic DNA as exemplified previously. Accordingly, the disclosure provides a method employing a plurality of polynucleotides wherein the plurality of target polynucleotides include a plurality of genomic nucleic acids.

In certain embodiments, the target polynucleotides correspond to genomic DNA obtained from a subject having or suspected of having a disorder or disease. In other embodiments, the target polynucleotides correspond to genomic DNA obtained from a subject suspected of having a disorder or disease. Yet in other embodiments, the target polynucleotides correspond to genomic DNA obtained from a subject where there is no indication of having a disorder or disease. In the former embodiment, the methods of the disclosure can be used, for example, to confirm the presence of the disorder or disease. In the latter two embodiments, the methods of the disclosure can be used, for example, to determine the likelihood or prevalence of a disorder or disease.

The disorder or disease being tested can be any disorder or disease that can be genetically determined or assessed for prevalence or likelihood. Such disorders or diseases include all genetically inherited disorders or diseases as well as all disorders or diseases that can be caused by, or correlated with, a genetic alteration or a specific gene allele. Genetic alterations include, for example, one or more nucleic acid mutations. Such diseases or disorders are well known to those skilled in the art. For example, there are more than 19,000 known genes associated with genetic disorders or diseases (see, for example, GENECARDS, Weizmann Institute of Science, date of access Jan. 6, 2014. URL: genecards.org/cgi-bin/listdiseasecards.pl?type=full. The presence or absence of any or all of these genes or genetic mutations in a subject can be assessed employing, for example, genomic DNA from that subject in the methods of the disclosure.

Exemplary genetically inheritable disorders or diseases include cancer, Cystic Fibrosis, Down Syndrome, Duchenne Muscular Dystrophy, Hemophilia, neurofibromatosis, Tay-Sachs disease, Alzheimer, Parkinson's disease, Huntington's disease, Achondroplasia, Alpha-1 Antitrypsin Deficiency, Antiphospholipid Syndrome, Autism, Autosomal Dominant Polycystic Kidney Disease, Charcot-Marie-Tooth, Cri du chat, Crohn's Disease, Dercum Disease, Duane Syndrome, Factor V Leiden Thrombophilia, Familial Hypercholesterolemia, Familial Mediterranean Fever, Fragile X Syndrome, Gaucher Disease, Hemochromatosis, Hereditary Spherocytosis, Holoprosencephaly, Klinefelter syndrome, Marfan syndrome, Myotonic Dystrophy, Noonan Syndrome, Osteogenesis imperfect, Phenylketonuria, Poland Anomaly, Porphyria, Polycystic Kidney Disease, Primary Ciliary Dyskinesia, Progeria, Retinitis Pigmentosa, Rett Syndrome, Severe Combined Immunodeficiency (SCID), Sickle cell disease, Spinal Muscular Atrophy, Thalassemia, Trimethylaminuria, Turner Syndrome, Variegate Porphyria, Velocardiofacial Syndrome, WAGR Syndrome and Wilson Disease.

Exemplary cancers include breast cancer, bladder cancer, colon cancer, colorectal cancer, gastric cancer, gastrointestinal stromal tumor, inflammatory myofibroblastic tumor, kidney cancer, leukemia, lymphoma, lung cancer, retinoblastoma, skin cancer including melanoma, prostate cancer, neurofibromatosis, ovarian cancer, rhabdomyosarcoma and thyroid cancer.

One useful source of genomic DNA from a subject to determine the presence, absence or predisposition of a genetic disorder or disease includes cfDNA. Cell free DNA is well known in the art. For example, in addition to the well known presence of fetal nucleic acids in the maternal circulation, it is also well known in the art that other nucleic acids can be isolated and amplified from serum. In this regard, Mulcahy et al., *LANCET* 348: 628 (1996), *Cancer and Mutant DNA in Blood Plasma*, reviewed, inter alia, several reports that showed the presence of circulating DNA in the plasma (Chen et al.) and serum (Narwoz et al.) of cancer patients and also pointed out that the occurrence of freely circulating genetic material with increased amounts having been described in subjects with cancer as well as autoimmune diseases. Moreover, the finding of cell free circulating DNA also is not unique to disease states. Emanuel and Pestka, *GATA* 10(6):144-146 (1993), *Amplification of Specific Gene Products from Serum* describe the presence of free DNA in serum of healthy individuals and in amounts sufficient to perform genetic analysis by PCR. In addition, Shapiro, *Determination of Circulating DNA Levels in Patients with Benign or Malignant Gastrointestinal Disease, Cancer* 51(11):2116-20 (1983), report that serum DNA concentration is markedly elevated in malignancy and moderately elevated in benign gastrointestinal disease.

Accordingly, the disclosure provides a method for determining the presence of a cancer associated gene. The method includes: (a) contacting a nucleic acid sample including a plurality of target polynucleotides with at least one primer under conditions sufficient for hybridization, the at least one primer containing an adapter; (b) amplifying by polymerase chain reaction (PCR) the plurality of target polynucleotides to produce a plurality of amplicons; (c) directly contacting a plurality of target specific capture primers specific to one or more different cancers immobilized on a solid support with the plurality of amplicons under conditions sufficient for hybridization to produce a first plurality of immobilized amplicons, the solid support further comprising a plurality of universal capture primers; (d) extending the plurality of target specific capture primers to produce a plurality of immobilized extension products complementary to the target polynucleotides; (e) annealing the plurality of universal capture primers to the plurality of the immobilized extension products; (f) amplifying by PCR the plurality of immobilized extension products to produce a second plurality of immobilized amplicons, wherein the population of immobilized amplicons includes a uniformity of 85% or more, and (g) sequencing the second plurality of immobilized extension products to determine the presence or absence of a cancer associated gene. The plurality of target polynucleotides can be 10 ng or less input nucleic acid and the input nucleic acid can be cfDNA.

The target polynucleotide molecules can be treated chemically or enzymatically either prior or subsequent to any of the methods described herein. In the methods described herein, the nucleic acid samples can be fragmented or can be used without fragmentation. The samples can be subjected to an amplification prior to use, for example a whole sample amplification technique such as random primer extension.

The plurality of target polynucleotides can be contacted with at least one primer. FIG. 1, panel 1, illustrates an exemplary configuration where each member in a plurality of target polynucleotides is contacted and hybridized to a pair of primers for amplification by polymerase chain reaction (PCR). As described further below, the target polynucleotides can be hybridized to a single primer when asymmetric PCR is desired. As illustrated in FIG. 1, panel 1, at least one primer also contains an adapter that can be used in, for example, downstream procedures. Accordingly, the disclosure provides a method of amplification using two primers and resulting in exponential amplification. One or both primers can contain an adapter. Also provided is a method of amplification wherein a plurality of target polynucleotides is amplified using one primer, resulting in asymmetrical amplification. The one primer can contain an adapter.

Generally amplification reactions employ two primers, often denoted forward and reverse primers. Amplification primers are typically single stranded polynucleotide structures. They can also contain a mixture of natural or non-natural bases and also natural and non-natural backbone linkages, provided, at least in some embodiments, that any non-natural modifications do not permanently or irreversibly preclude function as a primer. Amplification primers have the ability to anneal to a template polynucleotide strand during conditions of an extension or amplification reaction and to act as an initiation point for the enzymatic synthesis of a new polynucleotide strand complementary to the annealed template strand.

Primers can additionally include non-nucleotide chemical modifications, for example, to facilitate covalent attachment of the primer to a solid support if desirable. Certain chemical modifications can themselves improve the function of the molecule as a primer or can provide some other useful functionality, such as providing a cleavage site that enables the primer (or an extended polynucleotide strand derived therefrom) to be cleaved from a solid support. Useful chemical modifications can also provide reversible modifications that prevent hybridization or extension of the primer until the modification is removed or reversed.

The primers can be designed such that the 5' ends and the 3' ends carry a region of known sequence. The known sequence can be an universal sequence as the term is used herein and therefore have a common sequence among a plurality of oligonucleotides. Alternatively, for example, it can be a known, but unique sequence among a plurality of oligonucleotides. A universal sequence at can serve as a convenient site for the hybridization of a primer to enable the amplification of multiple different sequences using a single primer pair complementary to the universal sequence. Further, a universal sequence also can serve as an adapter complementary to, for example, a capture primer and allow immobilization of the adapter containing polynucleotide to the capture primer in embodiments where the capture primer is attached to a solid support. FIG. 1, panel 1, illustrates a universal sequence as an adapter as the thick portion on the bottom primers. The top primers also are illustrated as containing a sequence that does not hybridize with the target polynucleotide. This region can be a universal or other sequence and can have known or unknown sequence if it is a sequence other than a universal sequence.

In one embodiment, following hybridization of the at least one primer, the plurality of target polynucleotides can be subjected to amplification by, for example, PCR. The PCR amplification can be performed with a forward and reverse primer as illustrated in FIG. 1, panel 1, to result in exponential amplification of the target polynucleotides. The PCR amplification also can be performed with one primer to result in asymmetric or linear amplification of the target polynucleotides. Asymetric amplification is useful to produce single stranded amplicons of the plurality of target polynucleotides. The product of an amplification reaction described herein is referred to as an amplicon. Accordingly, amplification of a plurality target polynucleotides will produce a plurality of amplicons having the same nucleotide sequence has their template.

Although exemplified herein with general reference to PCR amplification reactions, given the teachings and guidance provided herein, those skilled in the art will know that other methods for amplifying nucleic acids, including various different types of PCR methods, are amendable to being used in the amplification steps disclosed herein. For example, amplification reactions that employ hybridization of an oligonucleotide to the target polynucleotide are useful in the amplification steps disclosed herein because they can include an adapter, for example, to allow hybridization to a capture primer. Such other amplification reactions, including different types of PCR methods include, for example, multiplex PCR, digital PCR (dPCR), dial-out PCR, allele-specific PCR, asymmetric PCR, helicase-dependent amplification, hot start PCR, ligation-mediated PCR, miniprimer PCR, multiplex ligation-dependent probe amplification (MLPA), nested PCR, quantitative PCR (qPCR), reverse transcription PCR (RT-PCR), solid phase PCR, ligase chain reaction, strand displacement amplification (SDA), transcription mediated amplification (TMA) and nucleic acid sequence based amplification (NASBA), as described in U.S. Pat. No. 8,003,354.

Multiplex methods for polynucleotide interrogation are particularly useful methods for manipulating and analyzing pluralities of target polynucleotides because they allow interrogation of many different species of target polynucleotides in a single reaction. Multiplex methods include, for example, multiplex amplification and multiplex sequencing. Other multiplex nucleic acid interrogation methods are well known in the art.

With exemplary reference to multiplex-PCR the multiplex amplification consists of multiple primer sets within a single target polynucleotide mixture to produce amplicons of varying sizes that are specific to different target polynucleotide sequences. By targeting multiple, different target polynucleotides simultaneously, sequence information can be obtained on a plurality of target polynucleotides from a single amplification reaction that otherwise would require several times the reagents and more time to perform. Annealing temperatures for each of target specific primer sets can be optimized to work correctly within a single reaction, and amplicon sizes (i.e., base pair length) can be the same or different length. Multiplexing kits for PCR are available commercially and are well known in the art. The number of different target polynucleotide species can vary depending on the desired application. For example, multiplex amplification can be performed on 25, 50, 150, 160, 170, 180, 190, 200, 210, 220, 230, 240, 250, 260, 270, 280, 290, 300, 320, 340, 360, 380, 400, 450, 500, 600, 700, 800, 900, 1000 or more different species of target polynucleotides. Multiplex amplification also can be performed on a plurality of target polynucleotides corresponding to any integer within the above range. Thus, the disclosure also provides a plurality of target polynucleotides having the above number or a larger number of different members of target polynucleotides, including a plurality of target polynucleotides having 200 or more different nucleotide sequences.

Accordingly, the disclosure provides a method of amplification of a plurality of target polynucleotides wherein the method includes multiplex amplification. The multiplex amplification can be multiplex PCR. The disclosure also provides a method of multiplex amplification having a multiplexcity of 180 or more different target polynucleotide species.

Other suitable methods for amplification of nucleic acids can include oligonucleotide extension and ligation, rolling circle amplification (RCA) (Lizardi et al., Nat. Genet. 19:225-232 (1998)) and oligonucleotide ligation assay (OLA) (See generally U.S. Pat. Nos. 7,582,420, 5,185,243, 5,679,524 and 5,573,907; EP 0 320 308 B1; EP 0 336 731 B1; EP 0 439 182 B1; WO 90/01069; WO 89/12696; and WO 89/09835,) technologies. As a non-limiting example of primer extension and ligation primers that can be specifically designed to amplify a nucleic acid of interest, the amplification can include primers used for the GoldenGate assay (Illumina®, Inc., San Diego, Calif.) as exemplified by U.S. Pat. Nos. 7,582,420 and 7,611,869.

Exemplary isothermal amplification methods that can be used in a method of the present disclosure include, but are not limited to, Multiple Displacement Amplification (MDA) as exemplified by, for example Dean et al., *Proc. Natl. Acad. Sci. USA* 99:5261-66 (2002) or isothermal strand displacement nucleic acid amplification exemplified by, for example U.S. Pat. No. 6,214,587, each of which is incorporated herein by reference in its entirety. Another non-PCR-based methods that can be used in the present disclosure include, for example, strand displacement amplification (SDA) which is described in, for example Walker et al., Molecular Methods for Virus Detection, Academic Press, Inc., 1995; U.S. Pat. Nos. 5,455,166, and 5,130,238, and Walker et al., Nucl. Acids Res. 20:1691-96 (1992) or hyperbranched strand displacement amplification which is described in, for example Lage et al., Genome Research 13:294-307 (2003). Isothermal amplification methods can be used with the strand-displacing Phi 29 polymerase or Bst DNA polymerase large fragment, 5'->3' exo⁻ for random primer amplification of genomic DNA. The use of these polymerases takes advantage of their high processivity and strand displacing activity. High processivity allows the polymerases to produce fragments that are 10-20 kb in length. As set forth above, smaller fragments can be produced under isothermal conditions using polymerases having low processivity and strand-displacing activity such as Klenow polymerase. Additional description of amplification reactions, conditions and components are set forth in detail in the disclosure of U.S. Pat. No. 7,670,810, which is incorporated herein by reference in its entirety.

Another nucleic acid amplification method that is useful in the present disclosure is Tagged PCR which uses a population of two-domain primers having a constant 5' region followed by a random 3' region as described, for example, in Grothues et al. Nucleic Acids Res. 21(5):1321-2 (1993). The first rounds of amplification are carried out to allow a multitude of initiations on heat denatured DNA based on individual hybridization from the randomly-synthesized 3' region. Due to the nature of the 3' region, the sites of initiation are contemplated to be random throughout the genome. Thereafter, the unbound primers can be removed and further replication can take place using primers complementary to the constant 5' region.

The above exemplary amplification methods can be employed to amplify one or more target polynucleotides, including a plurality of target polynucleotides. The target polynucleotides can be amplified in solution or immobilized on a solid support to produce a plurality of amplicons free in solution or a plurality of amplicons immobilized to a solid support.

The input amount for a plurality of target polynucleotides in an amplification reaction can range from micrograms (m) to nanograms (ng) or lower. In some embodiments, the starting amount for a plurality of target polynucleotides can be, for example, 100 µg or more of input nucleic acid. The starting amount also can be, for example, 10, 20, 30, 40, 50, 60, 70, 80 or 90 µg of input nucleic acid. In other embodiments, the starting amount of input nucleic acid can be in the nanogram range, including the low nanogram range. In such embodiments, the starting amount for a plurality of target polynucleotides can be, for example, 100 ng or less of input nucleic acid. The starting amount also can be, for example, 90, 80, 70, 60, 50, 40, 30, 20 or 10 ng or less of input nucleic acid. In other embodiments, the starting the starting amount for a plurality of target polynucleotides can be, for example, 9, 8, 7, 6, 5, 4, 3, 2, or 0.5 ng or less of input nucleic acid. The starting amount also can be any amount in between the above exemplary amounts. Accordingly, the disclosure provides a method wherein a plurality of target polynucleotides includes 10 ng or less input nucleic acid for an amplification reaction. Further, the plurality of target polynucleotides can be 1 ng input nucleic acid or 1 ng or less input nucleic acid for an amplification reaction.

In some embodiments, a plurality of immobilized target specific capture primers are contacted with a plurality of amplicons under conditions sufficient for hybridization. The target specific region of the target specific capture primers can be designed to anneal to one or more regions of a target polynucleotide. The hybridized target polynucleotide capture primers will become immobilized through the target specific capture primer.

FIG. 1, panel 2, exemplifies a plurality of target specific capture primers immobilized to a solid support. In this illustration, the target specific capture primers are longer than other capture primers immobilized to the solid support. Those skilled in the art will understand that it is inconsequential whether the target specific capture primers are longer, shorter or of the same length as other capture primers that are immobilized to the solid support. Rather, any capture primer will have a sequence necessary to perform its function. Target specific capture primers function to anneal, either selectively or specifically, to its target polynucleotide. Other capture primers such as certain universal capture primers function to anneal to a known sequence such as an adapter, primer binding site or other known sequence.

Each member within a plurality of target specific capture primer can have the same target specific sequence or a different target specific sequences. In the former embodiment, a plurality of target specific capture primers will anneal to and capture a plurality of the same species of target polynucleotides. In the latter embodiment, a plurality of target specific capture primers will anneal to and capture a plurality of different species of target polynucleotides. Generally, the target specific region of a capture primer is designed to be complementary to the same region for a particular member of a plurality of target polynucleotides. However, the target specific region also can be designed to be complementary to different nucleotide sequences within a particular target polynucleotide. Accordingly, given the teachings and guidance provided herein, those skilled in the art will understand what composition of members are to be included in a plurality of target specific capture primers are needed for a particular application.

The plurality of target specific capture primers can be large or small. Those skilled in the art will understand that a plurality of target specific capture primers will contain at least one target specific capture primer for each target polynucleotide that is desired to be captured. A plurality can also include multiple target specific capture primers to the same target polynucleotide species, including multiple target specific capture primers for some or all target polynucleotides species within a plurality of target polynucleotides. Accordingly, the disclosure provides a plurality of target specific capture primers that includes 2, 3, 4, 5, 6, 7, 8, 9, 10, 20, 30, 40, 50, 60, 70, 80, 90, 100 or 200 or more different members of the population. A plurality of target specific capture primers also can include, for example, 300, 400, 500, 1000, 5000, 10000, 50000, $1 \times 10^5$, $2 \times 10^5$, $3 \times 10^5$, $4 \times 10^5$, $5 \times 10^5$, $6 \times 10^5$, $7 \times 10^5$, $8 \times 10^5$, $9 \times 10^5$, $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$ or $1 \times 10^7$, or more different members. A plurality of target specific capture primers also can include all integer numbers in between the above exemplary population numbers. Accordingly, the disclosure provides a plurality of target specific capture primers having 200 or more different nucleotide sequences.

The plurality of target specific capture primers can be immobilized to a solid support as illustrated in FIG. 1, panel 2. The plurality of target specific capture primers also can be used free in solution and subsequently immobilized to a solid support by, for example, hybridization to a capture primer having a universal sequence complementary to a second region on the target specific capture primer.

In the specific embodiment where the plurality of target specific capture primers are first immobilized to a solid support as exemplified in FIG. 1, panel 2, the target specific capture primers can be attached directly to the solid support as illustrated. Alternatively, the target specific capture primers can be generated on the solid support from universal capture primers. In this regard, the thicker portion of the capture primers represent a universal sequence that are pre-seeded to a solid support. A target specific capture primer or a plurality of target specific capture primers having a complimentary region to the universal primer can be, for example, annealed to the universal capture primer and then extended to produce the full length target specific capture primer or plurality of target specific capture primers as illustrated in FIG. 1, panel 2.

Embodiments employing immobilized target specific capture primers are useful because they allow for normalization of a plurality of amplicons. For example, the solid support can be generated so that it contains a standard copy number of each species of target specific capture primers, thus, allowing capture of a standard copy number of target polynucleotides or amplicons thereof. The standard copy number of target specific capture primers can vary and can be designed so that a standard copy number of both abundant and rare target polynucleotide species are captured at equal frequency. In other embodiments, the different species of target specific capture primers are not standardized and can be immobilized in any desired ratio, including random. Given the teachings and guidance provided herein, those skilled in the art will know whether a standardized copy number, including an equal number copy number, or other ratio of different species of target specific capture primers are desirable for a particular use.

In addition to having a plurality of target specific capture primers, a solid support also can include a plurality of other types of capture primers as illustrated in FIG. 1, panel 2. The plurality of capture primers can have the same or different sequences. FIG. 1, panel 2, illustrates two pluralities of universal capture primers (filled and stippled thick sections of vertical oligonucleotide). In this exemplary embodiment, one plurality of universal capture primers is complementary to the adapter added to the plurality of target polynucleotides. The universal capture primers are useful for capturing, for example, a plurality of target polynucleotides or amplicons thereof containing the adapter. The universal capture primers also are useful, for example, for performing bridge amplification as illustrated in FIG. 1, panel 3, and described further below. A solid support can contain 1, 2, 3, 4, 5, 6, 7, 8, 9 or 10 or more different pluralities of universal capture primers.

Thus, the disclosure provides a plurality of target polynucleotides and/or amplicons thereof having an adapter that is complementary to a plurality of universal capture primers. The solid support can include a first, second or larger number of different pluralities plurality of universal capture primers. Also provided is a plurality of target specific capture primers further having a universal capture primer region. The universal capture primer region can have a nucleotide sequence corresponding to a first or second plurality of universal capture primers.

Accordingly, in some embodiments, the methods of this disclosure include providing a solid support having a plurality immobilized target specific capture primers. In some embodiments, providing a solid support includes immobilizing the target specific capture primer onto the solid support. In some embodiments, the plurality of target specific capture primers are immobilized directly onto the solid support.

In some embodiments, the target specific capture primer is assembled on the solid support in one or more steps. In some embodiments, the immobilization of a target specific capture primer includes immobilizing a universal capture primer onto the solid support. In certain embodiments, the immobilization of the target specific capture primer further includes converting the immobilized universal capture primer into the target specific capture primer. In certain embodiments the immobilization of the target specific capture primer further includes annealing a splint oligonucleotide with the universal capture primer, wherein the splint oligonucleotide includes a universal region complementary to a universal region of a target specific capture primer and a target specific region complementary to a target specific region in a target nucleotide. In certain embodiments, the immobilization of the target specific capture primer further includes extending the universal capture primer to produce a target specific capture primer.

In some embodiments, the target specific capture primer is immobilized in combination with other target specific capture primers. In some embodiments, the target specific capture primer includes a plurality of target specific capture primers. In some embodiments, the plurality of target specific capture primers includes only two types of target specific capture primers. For example, the target specific capture primers include either one of two universal capture regions, such as P5 or P7 regions and one target specific region. A P5 region includes the nucleotide sequence 5'-AATGATACGGCGACCACCGA-3'. A P7 region includes the nucleotide sequence 5'-CAAGCAGAA-GACGGCATACGA-3'. In certain embodiments, the oligonucleotide is the reverse complement of the P5 region sequence ("anti-P5": 5'-TCGGTGGTCGCCGTATCATT-3') or the P7 region sequence ("anti-PT": 5'-TCGTATGCCGTCTTCTGCTTG-3') capture primer. In certain embodiments, the oligonucleotide can hybridize with Illumina® capture primers P5 (paired end) (5'-AATGA-TACGGCGACCACCGAGAUCTACAC-3') or P7 (paired end) (5'-CAAGCAGAAGACGGCATACGA(8-oxo-G)AT-3'). In certain embodiments, the oligonucleotide can hybridize with the reverse complement of the Illumina® capture primer P5(paired end) ("anti-P5(paired end)": 5'-GTGTA-GATCTCGGTGGTCGCCGTATCATT-3') or P7(paired end) ("anti-P7(paired end)": 5'-ATCTCGTATGCCGTCTTCTGCTTG-3').

In other embodiments the plurality of target specific capture primers includes a population of different members. In certain embodiments, the population of target specific capture primers can include more than 10, 100, 1,000, 10,000, 100,000, 1,000,000, 10,000,000 different members. In certain embodiments, the target specific capture primers differ in the sequences included in the target specific capture regions. In certain embodiments, the target specific capture primers target different target polynucleotides.

In some embodiments of this disclosure, the immobilized target specific capture primer includes a plurality of immobilized target specific capture primers and the target polynucleotide includes a plurality of target polynucleotides.

In some embodiments, essentially all immobilized capture primers are target specific capture primers. In other embodiments, the target specific capture primer is immobilized in combination with universal capture primers. In certain embodiments, an excess of target specific capture primers is immobilized. In certain embodiments, the excess of target specific capture primers over universal capture primers is greater than 2:1, 3:1, 5:1, 10:1, 50:1, 100:1, 500:1, 1,000:1, 10,000:1, 50:000:1 or 100,000:1. In certain embodiments, an excess of universal capture primers is immobilized. In certain embodiments, the excess of universal capture primers over target specific capture primers is greater than 2:1, 3:1, 5:1, 10:1, 50:1, 100:1, 500:1, 1,000:1, 10,000:1, 50:000:1 or 100,000:1.

In certain embodiments directed to determining the presence, absence or susceptibility of a genetic disorder or disease, the plurality of target specific capture primers can be directed to one or more genes associated with such genetic disorders or diseases. Such genetic disorders or diseases include any of those exemplified previous or well known in the art. For example, a plurality of target specific capture primers can be directed to two or more disorders to detect the presence, absence or susceptibility of multiple different disorders or diseases. Thus, a panel of target specific capture primers can be utilized to detect multiple different diseases. The panel can include members within a plurality of target specific capture primers that are specific to 2, 3, 4, 5, 6, 7, 8, 9, 10, 20, 30, 40, 50, 60, 70, 80, 90, 100 or 200 or more genes associated with different or the same genetic disorder or disease.

By way of exemplification with reference to a panel of genes associated with cancer, a plurality of target specific capture primers can include any combination of the following cancer associated genes, including all combinations and/or permutations: AKT1, CTNNB1, FLT3, KRAS, PTPN11, SRC, ALK, EGFR, GNAS, MLH1, RB1, STK11, ATM, ERBB2, HNF1A, MPL, RAD50, TP53, BRAF, ERBB4, IDH1, NRAS, RET, VHL, BRCA1, FBXW7, JAK3, PIK3CA, SMAD4, CDH1, FGFR2, KIT, PTEN, SMARCB1, ABL1, CSF1R, GNA11, JAK2, NOTCH1, SMO, APC, FGFR1, GNAQ, KDR, NPM1, CDKN2, FGFR3, HRAS, MET and/or PDGFRA.

Accordingly, the disclosure provides a method for determining the presence of a cancer associated gene wherein a plurality of target specific capture primers include two or more different nucleotide sequences selected from the following genes: AKT1, CTNNB1, FLT3, KRAS, PTPN11, SRC, ALK, EGFR, GNAS, MLH1, RB1, STK11, ATM, ERBB2, HNF1A, MPL, RAD50, TP53, BRAF, ERBB4, IDH1, NRAS, RET, VHL, BRCA1, FBXW7, JAK3, PIK3CA, SMAD4, CDH1, FGFR2, KIT, PTEN, SMARCB1, ABL1, CSF1R, GNA11, JAK2, NOTCH1, SMO, APC, FGFR1, GNAQ, KDR, NPM1, CDKN2, FGFR3, HRAS, MET and PDGFRA. The plurality of target specific capture primers can be nucleotide sequences for each of the following genes: AKT1, CTNNB1, FLT3, KRAS, PTPN11, SRC, ALK, EGFR, GNAS, MLH1, RB1, STK11, ATM, ERBB2, HNF1A, MPL, RAD50, TP53, BRAF, ERBB4, IDH1, NRAS, RET, VHL, BRCA1, FBXW7, JAK3, PIK3CA, SMAD4, CDH1, FGFR2, KIT, PTEN, SMARCB1, ABL1, CSF1R, GNA11, JAK2, NOTCH1, SMO, APC, FGFR1, GNAQ, KDR, NPM1, CDKN2, FGFR3, HRAS, MET and PDGFRA.

In some embodiments, a plurality of amplicons is directly applied or contacted to a plurality of target specific capture primers following an amplification procedure including, for example, directly contacting a plurality of target specific capture primers immobilized to a solid support. Accordingly, the plurality of amplificons can be applied to a plurality of capture primers without a significant intervening purification step and can be a partially or substantially unpurfied plurality of amplicons. In this embodiment, the plurality of amplicons can therefore include in the mixture cellular components, including a high ration of cellular components, primers, amplification enzymes and unamplified or incorrectly amplified polynucleotides.

In other embodiments, a plurality of amplicons can be purified, either partially or completely, prior to contacting a plurality of target specific capture primers. Such nucleic acid purification procedures are well known to those skilled in the art and include, for example, precipitation, filtration and chromatography to remove cellular components such as macromolecules, salts and the like.

The conditions sufficient for hybridization of a plurality of target specific capture primers including, for example, a plurality of target specific capture primers immobilized on a solid support, can have an incubation or annealing period ranging from minutes to an hour or more. Shorter hybridization times are useful for efficiently proceeding to any subsequent step or steps in an integrated procedure. In some embodiments, the hybridization time can be, for example, 60 minutes or less. The hybridization time also can be, for example, 50, 45, 40, 35, 30, 25, 20, 19, 18, 17, 16, 15, 14, 13, 12, 11 or 10 minutes or less. The hybridization also can be, for example, shorter than 10 minutes including 9, 8, 7, 6 or 5 minutes for example. The hybridization time additionally be any period in between the above exemplary time periods. Accordingly, the disclosure provides a method wherein conditions sufficient for hybridization include incubation or annealing time of target specific capture primers to amplicons or other polynucleotides for 10 minutes or less.

In some embodiments, a plurality of amplicons can be double stranded prior to contacting to a plurality of target specific capture primers. To allow for annealing and capture by the target specific capture primers the plurality of amplicons can be denatured by, for example, high temperature or chemical reagents that that reduce Tm to separate the two strands of a double stranded polynucleotide. Stand separation, including partial strand separation, can be performed, for example, prior to or simultaneous with contacting a plurality target specific capture primers. In other embodiments, the plurality of amplicons can be single stranded. In such single strand embodiments a strand separation step is unnecessary, but can be usefully employed to remove secondary structures within the single strand.

Following amplicon capture by annealing to a target specific capture primer immobilized on a solid support to produce an immobilized plurality of amplicons, for example, the immobilized plurality of amplicons can be partially double stranded and partially single stranded. As illustrated in FIG. 1, panel 3, the left most immobilized amplicon is hybridized to a target specific capture probe and the non-complementary regions remain single stranded. An immobilized amplicon including an immobilized plurality of amplicons can be made double stranded by enzymatic extension from the target specific capture primer. Such a double stranded extension product is illustrated in the middle immobilized amplicon of FIG. 3, panel 3. Extension reactions are well known in the art and are exemplified further below and in the Examples.

In a next step according to a particular embodiment of the present disclosure, the immobilized plurality of amplicons can undergo further procedures. Such further procedures include amplification or sequencing, for example. In certain embodiments, the first plurality of immobilized amplicons are amplified using any of the previously described methods or other methods well known in the art to generate a second plurality of immobilized amplicons. When immobilized on a solid support, one particularly useful amplification procedure includes bridge amplification. As illustrated in FIG. 1, panel 3, the double stranded or partially double stranded amplicons produced from an extension reaction, for example, are denatured and the immobilized strand annealed to a universal capture primer through hybridization to an adapter as exemplified. The resulting structure is immobilized at both ends to create a bridge and the universal capture primer can be extended and then amplified using, for example, a universal primer region contained in the target specific capture primer. This second universal capture primer can be different than the first universal primer complementary to the adapter sequence. The strand that is not immobilized can, for example, be washed away. Accordingly, the method of the disclosure provides an amplification method that includes bridge amplification.

The bridge amplification methods described herein result in a uniform cluster or colony number for amplicons within a plurality. Cluster uniformity is illustrated in FIGS. 2 and 3, and described further below in the Examples. Accordingly, the disclosure provides a method of amplification of an immobilized polynucleotides wherein the uniformity includes 80, 81, 82, 83, 84, 85, 86, 87, 88, 89, 90, 91, 92, 93, 94 or 95 or more at 0.1 mean.

In bridge amplification, for example, suitable conditions are applied to the immobilized single stranded extension product, including an immobilized plurality of single stranded extension products, such that the single stranded extension product anneals to an immobilized universal capture primer to form a complex in the form of a bridge structure. Suitable conditions such as neutralising and/or hybridising buffers are well known in the art (See Sambrook and Russell, Molecular Cloning, A Laboratory Manual, third edition, Cold Spring Harbor Laboratory Press (2001)); Ausubel et al., Current Protocols in Molecular Biology, John Wiley and Sons, Baltimore, Md. (1998)). The neutralizing and/or hybridizing buffer can then be removed.

Next by applying suitable conditions for extension an extension reaction is performed. The amplification oligonucleotide of the complex is extended by sequential addition of nucleotides to generate an extension product complementary to the single stranded polynucleotide molecule. The resulting duplex is immobilised at both ends such that each strand is immobilised.

Suitable conditions such as extension buffers/solutions comprising an enzyme with polymerase activity are well known in the art (See Sambrook et al., supra; Ausubel et al. supra). This bridge amplification technique can be carried out as described, for example, in U.S. Pat. No. 7,115,400 and US 2005/0100900 A1, the contents of which are incorporated herein by reference.

Examples of enzymes with polymerase activity which can be used in the present disclosure are DNA polymerase (Klenow fragment, T4 DNA polymerase), heat-stable DNA polymerases from a variety of thermostable bacteria (such as Taq, VENT, Pfu, or Tfl DNA polymerases) as well as their genetically modified derivatives (TaqGold, VENTexo, or Pfu exo). A combination of RNA polymerase and reverse transcriptase can also be used to generate the extension products. Particularly the enzyme can in these and related embodiments have strand displacement activity, more particularly the enzyme can be active at a pH of about 7 to about 9, particularly pH 7.9 to pH 8.8, yet more particularly the enzymes are in certain exemplary embodiments Bst or Klenow.

The nucleoside triphosphate molecules used are typically deoxyribonucleotide triphosphates, for example dATP, dTTP, dCTP, dGTP, or are ribonucleoside triphosphates for example ATP, UTP, CTP, GTP. The nucleoside triphosphate molecules can be naturally or non-naturally occurring.

After the hybridization and extension steps, the support and attached nucleic acids can be subjected to denaturation conditions. A flow cell can be used such that, the extension buffer is generally removed by the influx of the denaturing buffer. Suitable denaturing buffers are well known in the art (See Sambrook et al., supra; Ausubel et al. supra). By way of example it is known that alterations in pH and low ionic strength solutions can denature nucleic acids at substantially isothermal temperatures. Formamide and urea form new hydrogen bonds with the bases of nucleic acids disrupting hydrogen bonds that lead to Watson-Crick base pairing. In a particular embodiment the concentration of formamide is 50% or more. These result in single stranded nucleic acid molecules. If desired, the strands can be separated by treatment with a solution of very low salt (for example less than 0.01 M cationic conditions) and high pH (>12) or by using a chaotropic salt (e.g. guanidinium hydrochloride). In a particular embodiment a strong base is used. A strong base is a basic chemical compound that is able to deprotonate very weak acids in an acid base reaction. The strength of a base is indicated by its pKb value, compounds with a pKb value of less than about 1 are called strong bases and are well known to one skilled in the art. In a particular embodiment the strong base is Sodium Hydroxide (NaOH) solution used at a concentration of from 0.05 M to 0.25 M, particularly 0.1 M.

Following the hybridization, extension and denaturation steps exemplified above, two immobilised nucleic acids will be present, the first containing a sequence the same as the first template single stranded polynucleotide molecule (that was initially immobilised) and the second being a nucleic acid complementary thereto, extending from one of the immobilised capture oligonucleotides. Both the immobilized strands are then able to initiate further rounds of amplification by subjecting the support to further cycles of hybridization, extension and denaturation. Thus the amplification proceeds from a single strand to a duplex, one duplex to two duplexes, two duplexes to four duplexes etc. throughout the cycles of annealing, extension and denaturation.

It can be useful to perform optional washing steps in between each step of the amplification method. For example an extension buffer without polymerase enzyme with or without dNTP's could be applied to the solid support before being removed and replaced with the full extension buffer.

Such further rounds of amplification can be used to produce a nucleic acid colony or cluster having multiple immobilized copies of the single stranded polynucleotide sequence and its complementary sequence.

The initial immobilization of an amplicon means that the extension product can hybridize with universal capture primers located at a distance within the total length of the template polynucleotide molecule. Once more copies of the immobilized extension products and its complement have been synthesized by carrying out further rounds of amplification, i.e. further rounds of hybridization, extension and denaturation, then the boundary of the nucleic acid colony or cluster being generated will be able to be extended further.

Accordingly, a method of the present disclosure allows the generation of a second plurality of immobilized amplicons or polynucleotide colonies from a first plurality multiple immobilized single stranded amplicons and that the density of these colonies can be controlled by altering the proportions of universal capture primers immobilized on a solid support.

In one particular aspect, a method of the disclosure is used to prepare clustered arrays of nucleic acid colonies, analogous to those described in U.S. Pat. No. 7,115,400, US 2005/0100900 A1, WO 00/18957 and WO 98/44151, by solid-phase amplification.

Clustered arrays formed by the methods of the disclosure are suitable for use in applications usually carried out on ordered arrays such as micro-arrays. Such applications by way of non-limiting example include hybridization analysis, gene expression analysis, protein binding analysis, sequencing, genotyping, nucleic acid methylation analysis and the like. The clustered array can be sequenced before being used for downstream applications such as, for example, hybridization with fluorescent RNA or binding studies using fluorescent labeled proteins.

As illustrated in FIG. 1, panel 4, the disclosure also encompasses methods of sequencing amplified nucleic acids generated by solid-phase amplification. Thus, the disclosure provides a method of nucleic acid sequencing including amplifying a plurality of immobilized extension products using solid-phase amplification as described above and carrying out a nucleic acid sequencing reaction to determine the sequence of the whole or a part of at least one amplified nucleic acid strand produced in the solid-phase amplification reaction.

In certain embodiments, the methods disclosed herein for obtaining the sequences of a plurality of different target polynucleotides can be performed in a sequential or integrated fashion that result in short start-to-finish times. For example, using the methods described herein, the sequence of a plurality of target polynucleotides can be determined in 3 hours or less for 50 sequencing cycles. The start-to-finish times also can be, for example, 2.9, 2.8, 2.7, 2.6 or 2.5 hours or less for 50 sequencing cycles. The integrated method includes, for example, starting with 10 ng or less of input nucleic acid; amplifying a plurality of target polynucleotides to produce a plurality of amplicons; capture of the plurality of amplicons to produce a first plurality of immobilized amplicons; amplifying the first plurality of immobilized amplicons to produce a second plurality of immobilized amplicons, and sequencing the amplicons for at least 50 sequencing cycles. Those skilled in the art will understand that the start-to-finish time for obtaining the sequences for a plurality of target polynucleotides will be similarly efficient, but longer when more sequencing cycles are performed. For example, 50 sequencing cycles takes about 2 hours and can result in an overall start-to-finish time of about 2 hours 50 minutes whereas 150 sequencing cycles takes about 4.5 hours and can result in an overall start-to-finish time of between about 5-6 hours.

Sequencing can be carried out using any suitable sequencing technique. A particularly useful method is one wherein nucleotides are added successively to a free 3' hydroxyl group, resulting in synthesis of a polynucleotide chain in the 5' to 3' direction. The nature of the nucleotide added can be determined after each nucleotide addition or at the end of the sequencing process. Sequencing techniques using sequencing by ligation, wherein not every contiguous base is sequenced, and techniques such as massively parallel signature sequencing (MPSS) where bases are removed from, rather than added to the strands on the surface are also within the scope of the disclosure.

For example, one useful sequencing method is sequencing-by-synthesis (SBS). In SBS, extension of a nucleic acid primer along a nucleic acid template (e.g. a target nucleic acid or amplicon thereof) is monitored to determine the sequence of nucleotides in the template. The underlying chemical process can be polymerization (e.g. as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template.

As described further below, flow cells provide a convenient solid support for housing amplified DNA fragments produced by the methods of the present disclosure. One or more amplicons in such a format can be subjected to an SBS or other detection technique that involves repeated delivery of reagents in cycles. For example, to initiate a first SBS cycle, one or more labeled nucleotides, DNA polymerase, etc., can be flowed into/through a flow cell that houses one or more amplified nucleic acid molecules. Those sites where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with amplicons produced by the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. Nos. 6,210,891; 6,258,568 and 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be adapted for application of pyrosequencing to amplicons produced according to the present disclosure are described, for example, in WIPO Pat. App. Ser. No. PCT/US11/57111, US 2005/0191698 A1, U.S. Pat. Nos. 7,595,883, and 7,244,559, each of which is incorporated herein by reference.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides (ZMWs). Techniques and reagents for FRET-based sequencing are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

Another useful sequencing technique is nanopore sequencing (see, for example, Deamer et al. Trends Biotechnol. 18, 147-151 (2000); Deamer et al. Acc. Chem. Res. 35:817-825 (2002); Li et al. Nat. Mater. 2:611-615 (2003), the disclosures of which are incorporated herein by reference). In some nanopore embodiments, the target nucleic acid or individual nucleotides removed from a target nucleic acid pass through a nanopore. As the nucleic acid or nucleotide passes through the nanopore, each nucleotide type can be identified by measuring fluctuations in the electrical conductance of the pore. (U.S. Pat. No. 7,001,792; Soni et al. Clin. Chem. 53, 1996-2001 (2007); Healy, Nanomed. 2, 459-481 (2007); Cockroft et al. J. Am. Chem. Soc. 130, 818-820 (2008), the disclosures of which are incorporated herein by reference).

Exemplary methods for array-based expression and genotyping analysis that can be applied to detection according to the present disclosure are described in U.S. Pat. Nos. 7,582,420; 6,890,741; 6,913,884 or 6,355,431 or US Pat. Pub. Nos. 2005/0053980 A1; 2009/0186349 A1 or US 2005/0181440 A1, each of which is incorporated herein by reference.

The products of solid-phase amplification reactions wherein both forward and reverse amplification oligonucleotides are covalently immobilized on the solid surface are so-called bridged structures as described above. In order to provide more suitable templates for nucleic acid interrogation procedures such as sequencing, for example, it can be useful to remove or displace substantially all or at least a portion of one of the immobilized strands in the bridged structure in order to generate a template which is at least partially single-stranded. The portion of the template which is single-stranded will thus be available for hybridization to a sequencing primer. The process of removing all or a portion of one immobilized strand in a bridged double-stranded nucleic acid structure can be referred to herein as linearization, and is described in further detail in WO07010251 and US20090118128, the contents of which are incorporated herein by reference in their entirety.

Bridged template structures can be linearized by cleavage of one or both strands with a restriction endonuclease or by cleavage of one strand with a nicking endonuclease. Other methods of cleavage can be used as an alternative to restriction enzymes or nicking enzymes, including inter alia chemical cleavage (e.g., cleavage of a diol linkage with periodate), cleavage of abasic sites by cleavage with endonuclease (for example USER, as supplied by NEB, Ipswich, Mass., USA, part number M5505S), or by exposure to heat or alkali, cleavage of ribonucleotides incorporated into amplification products otherwise comprised of deoxyribonucleotides, photochemical cleavage or cleavage of a peptide linker.

Following the cleavage step, regardless of the method used for cleavage, the product of the cleavage reaction can be subjected to denaturing conditions in order to remove the portion (s) of the cleaved strand (s) that are not attached to the solid support. Suitable denaturing conditions, for example sodium hydroxide solution, formamide solution or heat, will be apparent to the skilled reader with reference to standard molecular biology protocols (Sambrook et al., supra; Ausubel et al. supra). Denaturation results in the production of a sequencing template which is partially or substantially single-stranded. A sequencing reaction can then be initiated by hybridization of a sequencing primer to the single-stranded portion of the template.

A variety of solid supports are available for use in the methods of this disclosure. For example, some embodiments, the solid support comprises a patterned surface suitable for immobilization of capture primers in an ordered pattern. A "patterned surface" refers to an arrangement of different regions in or on an exposed layer of a solid support. For example, one or more of the regions can be features where one or more capture primers are present. The features can be separated by interstitial regions where capture primers are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or interstitial regions. In some embodiments, the capture primers are randomly distributed upon the solid support. In some embodiments, the capture primers are distributed on a patterned surface. Exemplary patterned surfaces that can be used in the methods and compositions set forth herein are described in U.S. Ser. No. 13/661,524 or US Pat. App. Publ. No. 2012/0316086 A1, each of which is incorporated herein by reference.

In some embodiments, the solid support comprises an array of wells or depressions in a surface. This may be fabricated as is generally known in the art using a variety of techniques, including, but not limited to, photolithography, stamping techniques, molding techniques and microetching techniques. As will be appreciated by those in the art, the technique used will depend on the composition and shape of the array substrate.

The composition and geometry of the solid support can vary with its use. In some embodiments, the solid support is a planar structure such as a slide, chip, microchip and/or array. As such, the surface of a substrate can be in the form of a planar layer. In some embodiments, the solid support comprises one or more surfaces of a flowcell. The term "flowcell" as used herein refers to a chamber comprising a solid surface across which one or more fluid reagents can be flowed. Examples of flowcells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

In some embodiments, the solid support or its surface is non-planar, such as the inner or outer surface of a tube or vessel. In some embodiments, the solid support comprises microspheres or beads. By "microspheres" or "beads" or "particles" or grammatical equivalents herein is meant small discrete particles. Suitable bead compositions include, but are not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and teflon, as well as any other materials outlined herein for solid supports may all be used. "Microsphere Detection Guide" from Bangs Laboratories, Fishers Ind. is a helpful guide. In certain embodiments, the microspheres are magnetic microspheres or beads.

The beads need not be spherical; irregular particles may be used. Alternatively or additionally, the beads may be porous. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller or larger beads may be used.

The disclosure also provides in certain embodiments a flow cell having one or more pluralities of capture primers immobilized thereto. One plurality can be a target specific capture primer. The target specific capture primer can include a universal primer region. Another plurality can be a universal capture primer. One or both of the above exemplary pluralities of capture primers can be immobilized to the flow cell.

Accordingly, the disclosure also relates to flow cells for the preparation of a plurality of amplicon clusters wherein the flow cells contain a coating of one or more pluralities of immobilized capture primers. Thus, a solid support as described herein can occur within or as a part of a flow cell and the methods set forth herein can be carried out in a flow cell. The one or more pluralities of capture primers can be coated over the whole of the flow cell surface rather than in discreet locations that comprise different sequences in each small location. The flow cell can be of a size of 1 cm$^2$ or greater whereby the whole 1 cm$^2$ or greater includes a coating of multiple copies of capture primers for each of the one or more pluralities of capture primers. A flow cell can be distinguished from, for example, a spotted array or photolithographically synthesised array due to the fact that the oligonucleotides are attached to each and every surface; top, bottom, walls and ends of the flow cell chamber, rather than being an array on a single planar surface. However, if desired a flow cell that is used in a method set forth herein can have surfaces with different reactivity for oligonucleotides such that the oligonucleotides are only attached to one or a subset of the aforementioned surfaces or even to only a subset of regions within these surfaces.

The flow cell can in certain embodiments be coated with three pluralities of capture primers species of different sequence composition, namely two capture primer species and a target specific capture primer as illustrated in FIG. 1, panel 3. Further, the target specific capture primer can include a universal primer region having the same sequence as one of the two plurality of capture primers as illustrated in FIG. 1, panel 3. The flow cell can in certain embodiments be coated with no more than the three pluralities of capture primer species. However, in other particular embodiments, the flow cell can further include one or more other pluralities of capture primer species whether a universal capture primer, target specific capture primer or other species of capture primer. The target specific capture primer can be present at a lower concentration than the universal capture primer, for example at least 100, 1000 or 100,000 fold lower relative concentration. The two pluralities of universal capture primers can be present at similar ratios to each other, for example, varying by less than a factor of two. Given the teachings and guidance provided herein, those skilled in the art will know what configuration of universal capture primers and target specific capture primers to immobilize on a flow cell to achieve a desired result.

The disclosure also provides a method for increasing detection sensitivity of a nucleic acid sequence variant. The method includes: (a) contacting a nucleic acid sample including a plurality of target polynucleotides with gene specific forward and reverse primers under conditions sufficient for hybridization, each species of the gene specific forward primer including a unique sequence index and an adapter; (b) amplifying by polymerase chain reaction (PCR) the plurality of target polynucleotides to produce a plurality of amplicons; (c) directly contacting a plurality of target specific capture primers immobilized on a solid support with the plurality of amplicons under conditions sufficient for hybridization to produce a first plurality of immobilized of amplicons, the solid support further including a plurality of universal capture primers; (d) extending the plurality of target specific capture primers to produce a plurality of immobilized extension products complementary to the target polynucleotides; (e) annealing the plurality of universal capture primers to the plurality of the immobilized extension products; (f) amplifying by PCR the plurality of immobilized extension products to produce a second plurality of immobilized amplicons, wherein the second plurality of immobilized amplicons comprises a uniformity of 85% or more; (g) sequencing the second plurality of immobilized amplicons, and (h) eliminating random sequence errors for one or more target polynucleotide by comparing three or more nucleotide sequences at a variant position for a target polynucleotide species, wherein the target polynucleotide species are identified by the unique sequence index to thereby determine a true nucleotide sequence variant in the one or more target polynucleotides.

The methods described previously also can be employed to increase the detection sensitivity of a nucleic acid sequence variant. In nucleic acid amplification and sequencing it is important to distinguish sequencing errors resulting from polymerase infidelity in these procedures, for example, from the authentic sequence. This distinction is especially important to identify variant sequences that are naturally occurring in a sample. Distinguishing true sequence variants over random nucleotide sequence errors can be accomplished by associating a unique sequence barcode or index with each polynucleotide species within a plurality of target polynucleotides.

Figure 5:
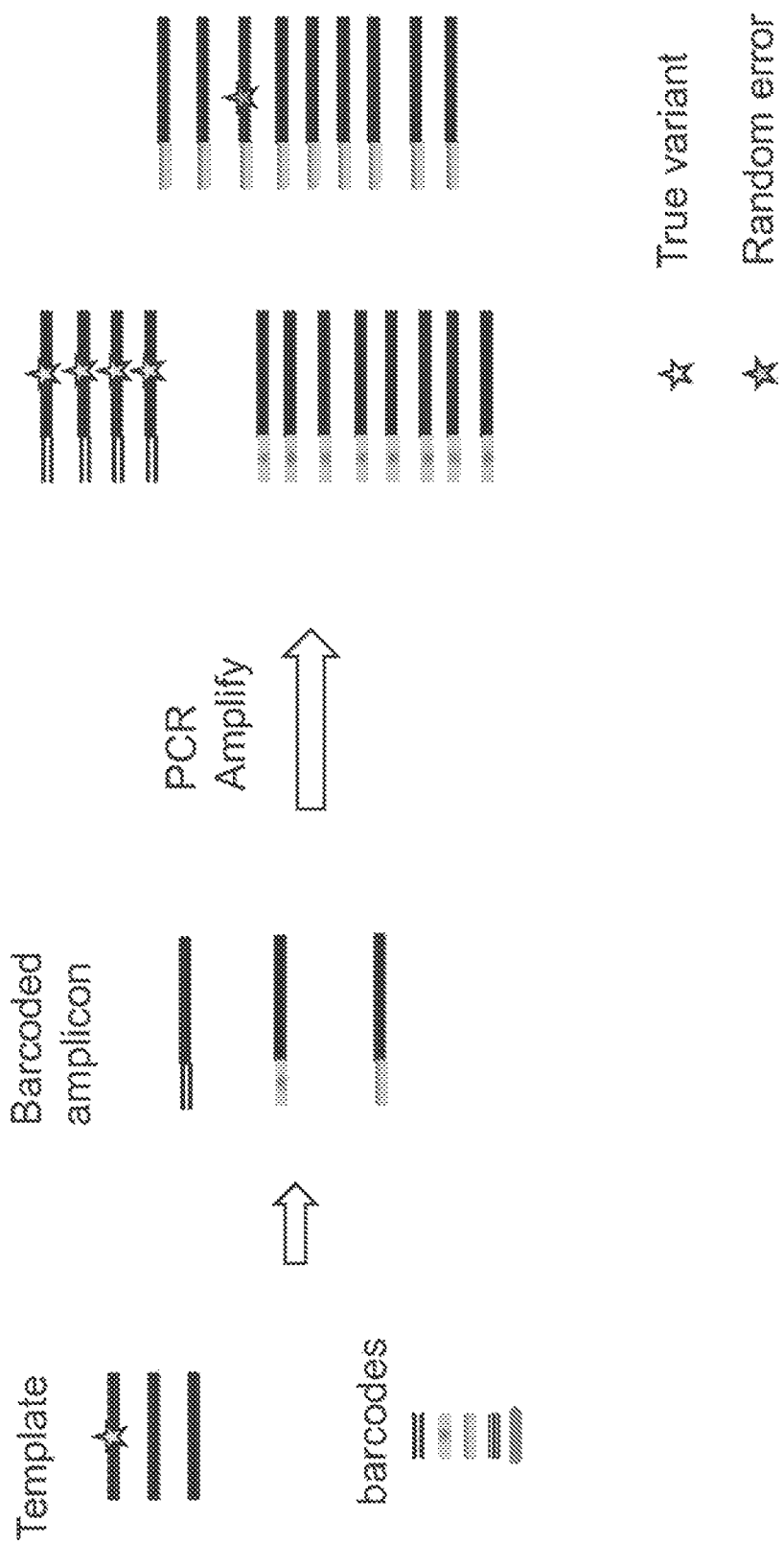
FIG. 5 is a schematic exemplifying the use of unique molecular barcodes or nucleotide indices to distinguish true nucleotide variants over random nucleotide sequencing errors.

FIG. 5 illustrates attachment of a unique index for each target polynucleotide species. FIG. 5 shows a plurality of target polynucleotides (identified therein as "Template"). For purposes of illustration, the plurality consists of three members where one member is a true nucleotide variant (light star). A unique barcode is added to each member and the plurality is amplified to result in three pluralities of amplicons each derived from the uniquely barcoded original member. The origin of the three pluralities can be identified by sequencing and identifying the barcode. A comparison of the members within each plurality shows the variant occurring in each or most members. In contrast, one plurality of amplicons contains a member having a sequence difference (dark star) compared to the remaining members of the amplicon plurality. Because the majority of the members within this plurality do not contain that nucleotide change its incorporation occurred by random error.

The above design also is applicable to identify true variants within a plurality of different target polynucletides. As disclosed herein, a target polynucleotide species refers to members of a plurality of target polynucleotides having the same sequence. In this embodiment, each target polynucleotide species is identified with the same unique index distinguishing that target polynucleotide species from other target polynucleotide species (and vice versa). Thus, target polynucleotides having the same sequence (i.e., species members) have the same index. Following amplification and sequencing species members can be identified by having the same index and the occurrence of a true variant compared to random error can be determined based on sequence comparison to other members within the plurality of species members.

Thus, the methods described previously can further include an index sequence within a gene specific primer used to amplify a target polynucleotide. Each gene specific primer will therefore contain a unique index that identifies its corresponding target polynucleotide. Accordingly, a plurality of gene specific primers corresponding to a plurality of different target polynucleotides can be employed to amplify the plurality of different target polynucleotides and result in incorporation of the uniquely identifying index into each resulting amplicon species within the plurality of amplicons thus produced.

The index can be a unique nucleotide sequence that is distinguishable from other indices. It can also be distinguishable from other nucleotide sequences within plurality polynucleotides either by sequence or location within the target polynucleotide. A nucleotide index can be a random or a specifically designed nucleotide sequence. An index can be of any desired sequence length so long as it is of sufficient length to be unique nucleotide sequence within a plurality of indices in a population and/or within a plurality of polynucleotides that are being analyzed or interrogated. In some embodiments, an index is a polynucleotide or region within a polynucleotide ranging from about 8-30 nucleotides. An index can be, for example, 10, 11, 12, 13, 14, 15, 16, 17, 18, 19, 20, 21, 22, 23, 24, 25, 26, 27, 28, 29 or 30 nucleotides or longer. For example, an index can be 35, 40, 45 or 50 nucleotides or longer.

Figure 7:
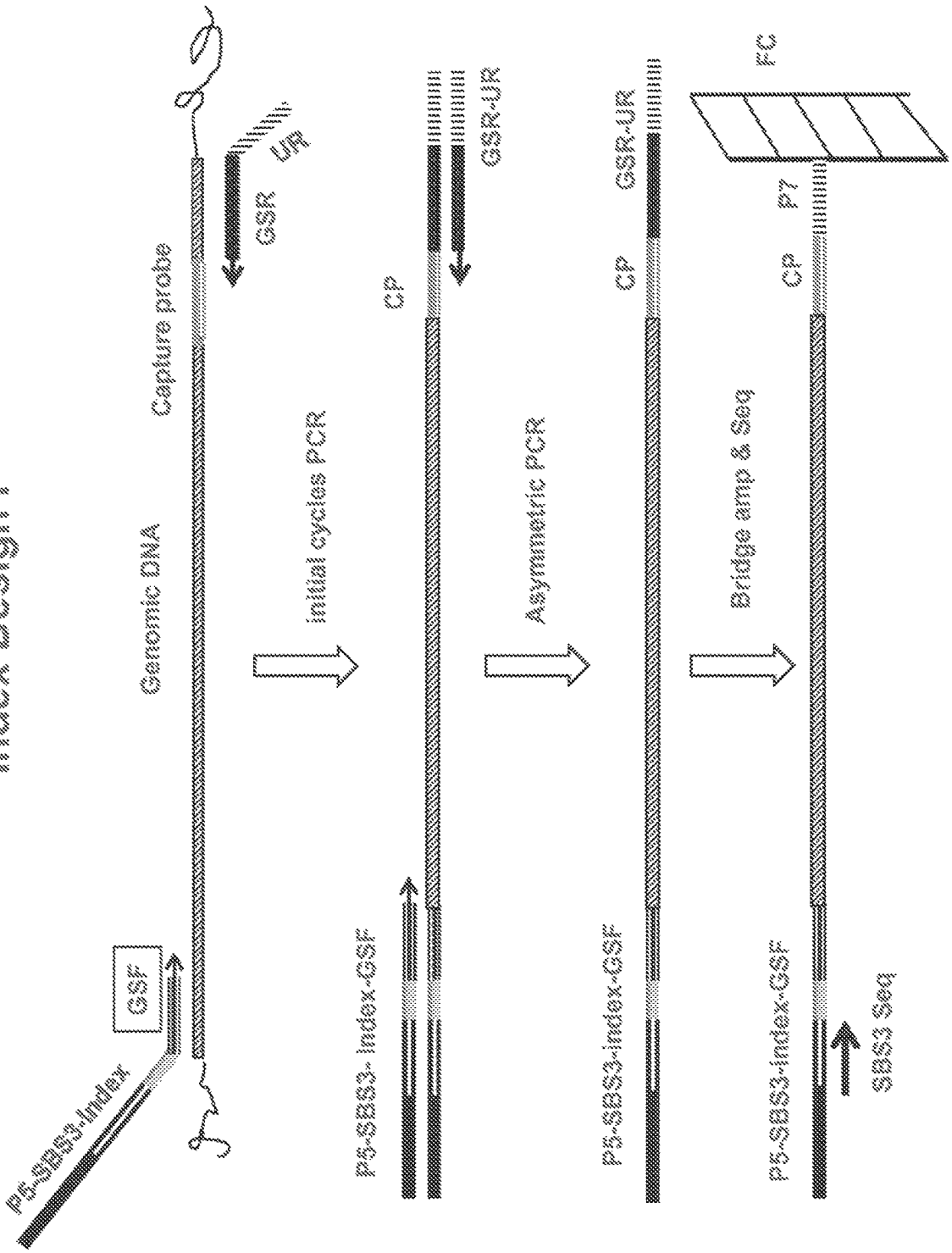
FIG. 7 is a schematic showing a one step incorporation of an index into a target polynucleotide through a target specific amplification primer where the index is downstream of a sequencing primer binding site.

FIG. 7 illustrates one exemplary gene specific primer design to incorporate an index into a target polynucleotide. In this embodiment, the index corresponds to the solid gray region on the gene specific forward primer (GSF). Amplification with a primer pair corresponding to the gene specific forward, containing the index, and a gene specific reverse primers as illustrated therein incorporates the index into the amplicon. FIG. 7 further illustrates continued amplification follow index incorporation by asymmetric amplification and subsequent bridge amplification and sequencing using a sequencing primer specific to a primer binding site also introduced by the GSF.

Figure 8:
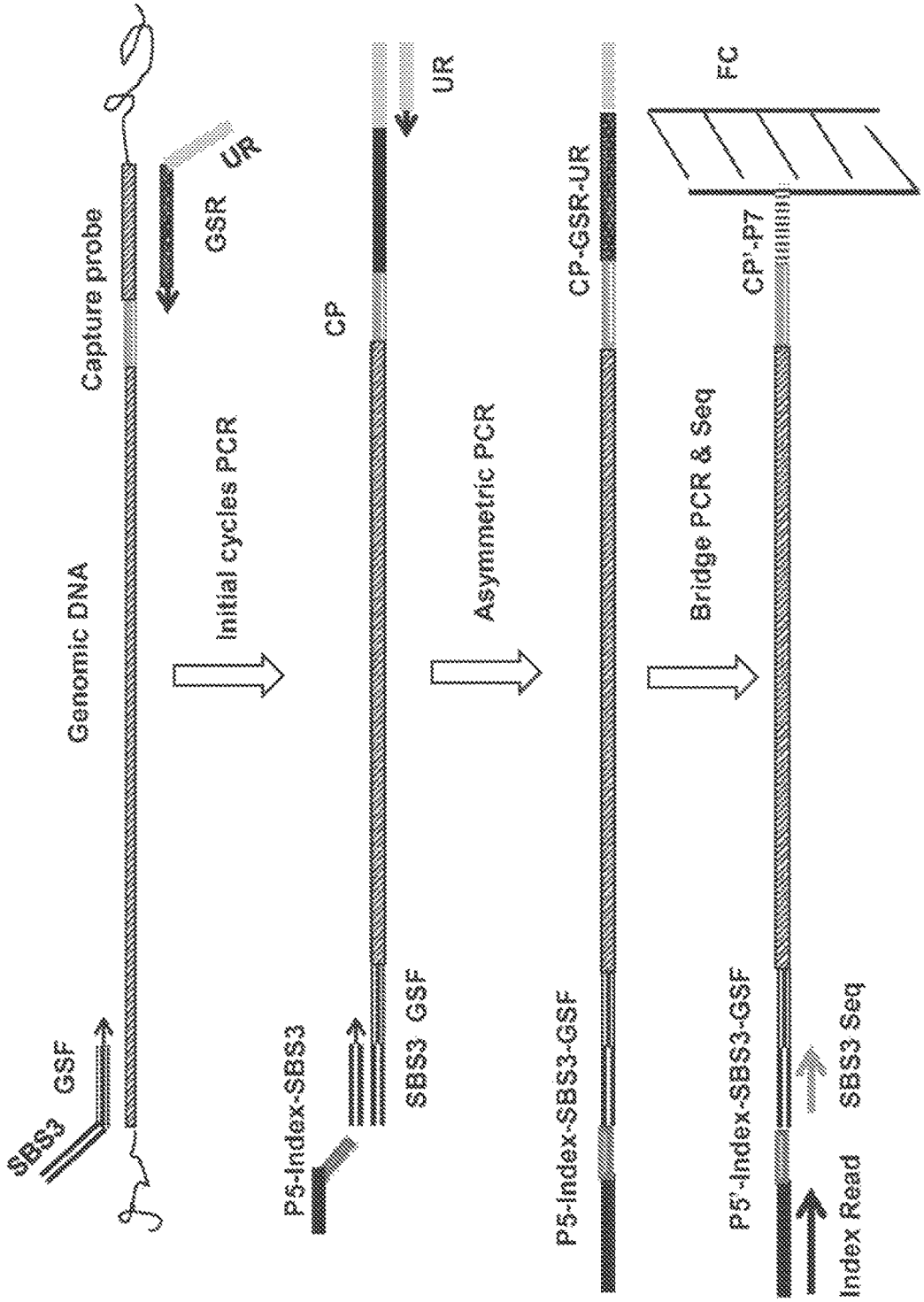
FIG. 8 is a schematic showing a two step incorporation of an index into a target polynucleotide through a sequencing primer where the index is upstream of the sequencing primer binding site.

FIG. 8 illustrates another exemplary gene specific primer design to incorporate an index into a target polynucleotide. In this embodiment, the index is incorporated in a second amplification step. For example, the initial amplification is performed with a pair of gene specific forward (GSF) and reverse (GSR) primers. One or both of the primers can contain a universal sequence region such as a primer binding site for subsequent rounds of amplication. In this embodiment, the index also corresponds to the solid gray region and, although it can be included in either of the subsequent round primers, it is illustrated to be in the primer that binds to the primer binding site incorporated by the GSF (SBS3 sequencing primer). Amplification with a primer pair corresponding to the primer containing the index and a reverse primer as illustrated therein incorporates the index into the amplicon. FIG. 8 further illustrates continued amplification follow index incorporation by asymmetric amplification and subsequent bridge amplification and sequencing using a sequencing primer specific to a primer binding site also introduced by the primer used in the subsequent round of amplification. This primer can also contain a second primer binding site such that it is upstream of the index for sequencing in tandem with the target polynucleotide.

Given the teachings and guidance provided herein, those skilled in the will know that all of the methods disclosed herein also can be performed with unique indices incorporated into a target specific capture primer to increase the detection sensitivity of nucleic acid sequence variants.

Accordingly, the methods of the disclosure provide a method for increasing detection sensitivity of a nucleic acid sequence variant, wherein the plurality of target polynucleotides includes 10 ng or less input nucleic acid. The method can have conditions sufficient for hybridization to include incubation for 10 minutes or less. The method further includes detecting a mismatch rate of 0.3% or less for a variant nucleotide position.

Also provided is a method for increasing detection sensitivity of a nucleic acid sequence variant, wherein contacting step a nucleic acid sample having a plurality of target polynucleotides includes a first round of PCR amplification with a first gene specific forward and a reverse primers and a second round of PCR amplification with a second forward primer complementary to a portion of the first gene specific forward primer, the second forward primer including the unique sequence index and the adapter. The adapter can be complementary to a plurality of universal capture primers. The universal capture primers can be immobilized to a solid support.

Further provided is a method for increasing detection sensitivity of a nucleic acid sequence variant, wherein the amplification of the plurality of target polynucleotides includes asymmetrical PCR. The amplification of the plurality of target polynucleotides also can includes multiplex amplification. The multiplex amplification includes a multiplexicity of 180 or more.

Yet further provided is a method for increasing detection sensitivity of a nucleic acid sequence variant, wherein the solid support further includes a second plurality of universal capture primers. Further, the plurality of target specific capture primers can further include a universal capture primer region. The universal capture primer region can have a nucleotide sequence corresponding to or complementary to the second plurality of universal capture primers.

Also provided is a method for increasing detection sensitivity of a nucleic acid sequence variant, wherein the plurality of target specific capture primers include 200 or more different nucleotide sequences. The method includes sequence variant detection within a plurality of target polynucleotides include 200 or more different nucleotide sequences. The plurality of target polynucleotides can be a plurality of genomic nucleic acids.

Additionally provided is a method for increasing detection sensitivity of a nucleic acid sequence variant, amplification of immobilized extension products includes bridge amplification. The method includes a solid support wherein the solid support can be a flow cell.

Further provided is a method for increasing detection sensitivity of a nucleic acid sequence variant, wherein sequencing of a plurality of amplicons produced from an amplified plurality of target polynucleotide includes 50 sequencing cycles. The method includes a start-to-finish time of 3 hours or less.

It is understood that modifications which do not substantially affect the activity of the various embodiments of this disclosure are also included within the definition of the disclosure provided herein. Accordingly, the following examples are intended to illustrate but not limit the present disclosure.

Example I

Amplicon Preparation and Sequencing Procedure

This Example describes an integrated procedure for amplicon preparation and target polynucleotide sequencing.

Briefly, sample genomic DNA was added to a PCR reaction mixture in a 100 µl total volume containing 50 µl of KAPA 2× 2G multiplex PCR buffer (Kapa Biosystems, Wilmington, Mass.), 0.5 µM of forward primer mix (F), 0.02 µM of reverse primer mix (R), 20 units of KAPA 2G Hot Start Enzyme (buffer (Kapa Biosystems, Wilmington, Mass.) and water. Amplification was performed using the following PCR program: incubation at 95° C. for 1 minute (min) followed by 30 cycles of the following incubations: (1) 97° C. for 5 seconds (sec); (2) 58° C. for 45 sec; (3) 72° C. for 1 min, and (4) hold at 4° C. The PCR products were subsequently sequenced after immobilization and clustering to a flow cell as described below.

Capture probe extension, targeted clustering of the above PCR products and sequencing was performed using an MiSeq benchtop sequencer (Illumina, San Diego, Calif.).

For this procedure, a MiSeq kit cartridge (Illumina, San Diego, Calif.) was thawed in water approximately 30 min before the automated MiSeq run and the heat block was turned on to 95° C. Additionally, an HFE tube (600 µl (Illumina, San Diego, Calif.)) was thawed on ice and a solution of 0.1N NaOH 1 ml was prepared. PCR product (1000 was diluted with 400 ul HT1 buffer (Illumina, San Diego, Calif.) in an eppendorf tube. Similarly, the capture probe templates were prepared in 600 µl of HT1 buffer in a separate tube. Deionized water was added into the heat block wells and the above two tubes were inserted into wells with slow shaking (approximately 100 rpm) for 5 min. After the 5 min heat block incubation the tubes were placed on the ice for at least 2 min. The thawed MiSeq cartridge was inverted several times to disperse and re-settle the reagents down to the bottom. Reagents were loaded into the MiSeq cartridge as follows: PCR product was transferred into the #17 tube in the cartridge; capture probes were transferred into the #18 tube, HFE was loaded into into the #19 tube and 0.1N NaOH was added into the #20 tube. The MiSeq cartridge, MiSeq FC (Illumina, San Diego, Calif.) and PR2 (Illumina, San Diego, Calif.) bottle to MiSeq was set up on the MiSeq sequencer and the sequencing run process was started according to manufacturer's recommendation. The prepared samplesheet was loaded (Javelin v.51 chemistry) and the extension, targeted clustering and sequencing run was initiated after flow check step according to manufacturer's recommendations.

Capture probe extension, targeted clustering of the above PCR products and sequencing was also performed using a Genome Analyzer (Illumina, San Diego, Calif.).

For this procedure, the clustering and sequencing template was prepared by mixing HT1 buffer with PCR product in a 8-tube strip (1 to 10 µl of PCR product with 19 to 10 ul of HT1 buffer, respectively). Capture probes (3-500 pM) were prepared in another 8-tube strip. A thawed cBOT Paired End Cluster Plate v3 (Illumina, San Diego, Calif.) was placed onto cBOT automated clustering system and the procedure for capture probe extension and amplification was initiated using the run command (Run <Capture_Probe_Extension_Amp_LBH_v #> recipe). A set of standard Genome Analyzer (GA) sequencing reagents (Illumina, San Diego, Calif.) were thawed (IMX, LFN, CLM, SMX) and a whole tube content of the LFN was added into the IMX tube, followed by addition of HDP36 into the same IMX tube. The contents were mixed well. All reagents and buffers, including PR1, PR2, PR3 (Illumina, San Diego, Calif.), were placed onto the GA at their designated positions followed by priming all lines with reagents using the GA command <Prime_v #> recipe. The flowcell and prism were cleaned with an ethanol wipe and lens paper, respectively and the prism reinserted into the machine. The beam dump was lowered. The flowcell was properly positioned on top of the prism and the manifold was slowly lowered. Proper flow of reagent into the flowcell was confirmed by manually pumping 100 µl solution 5 (PR2) at an aspiration rate of 60 µl/min and a dispense rate of 2000 µl/min. Immersion oil (135 µl) was applied between the prism and flowcell. The instrument door was closed and the sequencing run was started with the GA command Run <GA2_40cyle_10rows_SR_v8.3> recipe.

Example II

Sequence Quality Resulting from the Integrated Preparation and Sequencing Procedure This Example describes a comparison of sequence uniformity and sequencing depth using various concentrations and types of input nucleic acid.

The procedures described in Example I were employed to prepare amplicons from populations of target polynucleotides and determine their sequence by multiplex sequencing. Shown in FIG. 2 are the results using 1 ng and 10 ng of input genomic DNA.

Uniformity was calculated based on the clusters of each amplicon from MiSeqReporter. The number of amplicons with clusters more than 0.1 mean, 0.2 mean, 0.3 mean 0.5 mean were counted. For example, at 0.2 mean, More than 80% of amplicons had more than 0.2 mean number of clusters.

For sequencing depth, the number of amplicons with more than 10/100/250/500 clusters were counted. For example, more than 80% of the amplicons had a coverage of at least 500×. Uniformity and coverage are the typical metrics people use to measure sequencing quality. The results shown in FIG. 2 demonstrated that a high sequencing quality can be achieved using 1 ng and 10 ng of genomic DNA.

Shown in FIG. 3 are the results using four different amounts of DNA obtained from formalin-fixed paraffin embedded tissue. The four different concentrations ranged from 1 ng to 50 ng as shown on in the figure.

The uniformity and sequencing depth results shown in FIG. 3 further demonstrated that a high sequencing quality can be achieved for a wide range of DNA obtained from Formalin-fixed paraffin embedded tissues. The cluster PF (Passing Filter) density, which indicates the number of clusters having a specified quality, was very good. Specificity is a measurement of how many reads are accurate. More than 90% specificity was achieved in this study.

Figure 4:
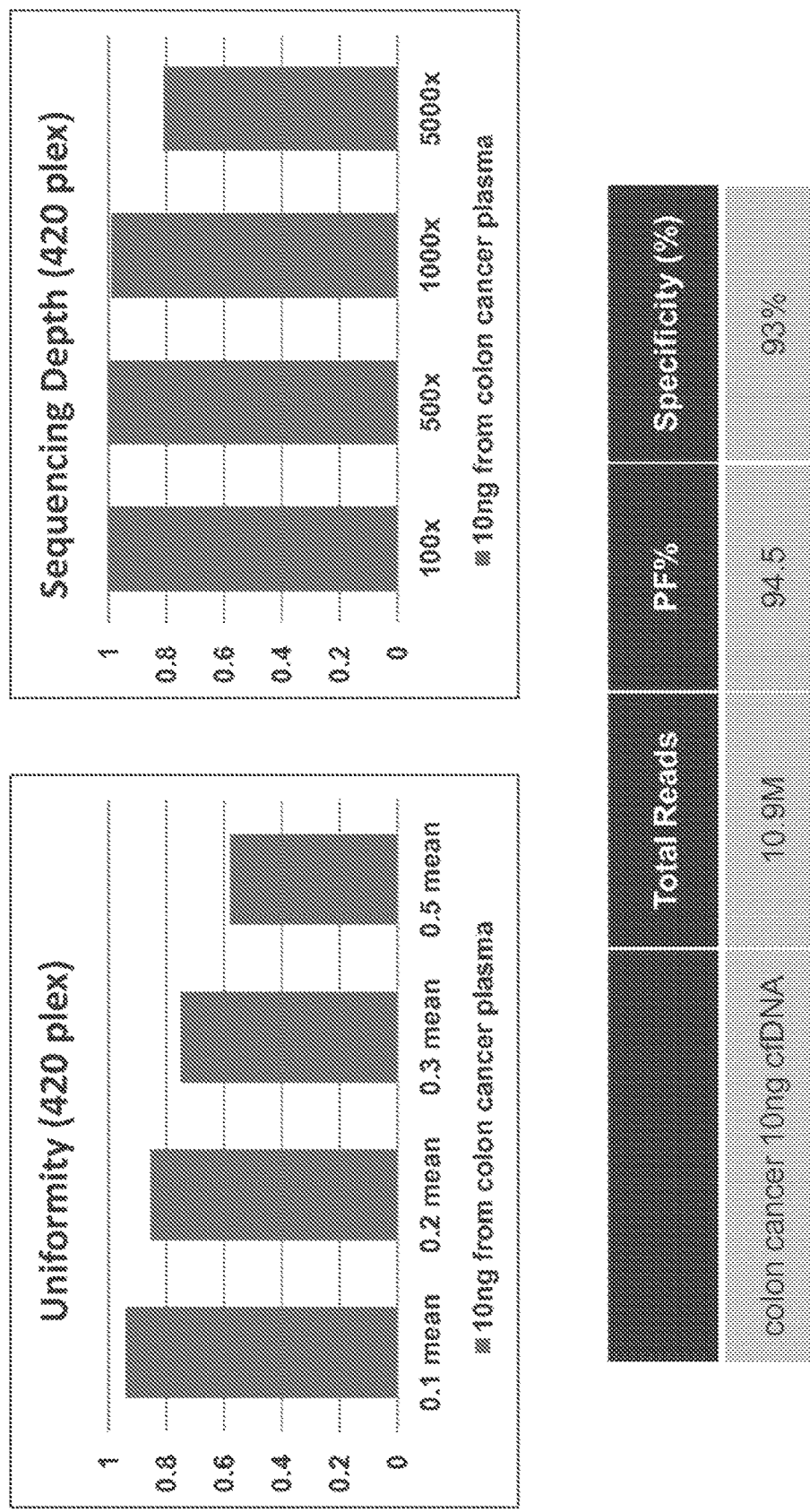
FIG. 4 shows a comparison of the sequencing uniformity and the sequencing depth for 10 ng of cell free DNA isolated from 1 ml of plasma for a multiplex sequencing run.

Additional studies were performed using cell free DNA (cfDNA) extracted from plasma from normal people as well as from cancer patient and obtained similar results. Shown in FIG. 4 are the results using 10 ng of cfDNA isolated from 1 ml of plasma.

As with FIGS. 2 and 3, uniformity similarly was calculated based on the clusters of each amplicon from MiSeqReporter. The number of amplicons with clusters more than 0.1 mean, 0.2 mean, 0.3 mean 0.5 mean were counted. At 0.2 mean, more than 80% of amplicons had more than 0.2 mean number of clusters.

Similarly, for sequencing depth, the number of amplicons with more than 10/100/250/500 clusters were counted. All of the amplicons had a coverage of at least 500×. Additionally, the cluster PF density and other parameters shown in the table inset also were very good. The results show a specificity of 93% was achieved, meaning that 93% of the clusters align to the correct targets. These results additionally demonstrate that a high sequencing quality can be obtained directly from cell free DNA isolated from plasma.

Example III

Detection Sensitivity Resulting from the Integrated Preparation and Sequencing Procedure This Example shows the detection accuracy of single mutations within a population of target polynucleotides.

A library was prepared and sequenced following the methods described herein using 1.65 ng of DNA obtained from Horizon Diagnostics in a 201 multiplex format (201 plex). The mutations listed in the following table were identified with the indicated frequency listed. This DNA has been verified to have certain frequency of mutations by Horizon Diagnostics using digital PCR. 1.65 ng is approximately 500 haploid genome copies. At 1% rate, approximately 5 copies of mutant are present. Therefore, this method is sensitive enough to detect 5 copies of a mutant in a population of diverse sequences.

| Simultaneous detection of multiple mutants* | | | | |
|---|---|---|---|---|
| Gene Name | Mutation | Mutant Type | Frequency verified by digital PCR | Frequency by Javelin** |
| BRAF | V600E | A->T | 10.5% | 10%, 11% |
| PI3KCA | E545K | G->A | 9% | 9%, 9% |
| KRAS | G12D | C->T | 6% | 6%, 8% |
| EGFR | L858R | T->G | 3% | 3%, 4% |
| EGFR | T790M | C->T | 1% | 1%, 1% |

*Reference genomic DNA with mutations are obtained from Horizon Diagnostics.
**Results from two independent experiments.

Example IV

Unique Molecular Indices for Determining True Sequence Variants from Errors

This Example describes the use of unique nucleotide indices to distinguish sequencing errors from authentic variants in a target polynucleotide sequence.

Unique Molecular Barcodes (UMB) or indices of random nucleotides (10-15N) were inserted between the sequencing primer region and the gene specific sequence region in the PCR forward primer. UMBs were introduced into the template DNA by performing 2-4 cycles of PCR with PCR primers with UMBs inserted. After 2-4 cycles, residual UMB primers were removed using exonuclease 1 treatment and SPRI beads clean up. Additional 30-35 cycles of PCR were performed using primers composed of universal adaptor sequence. Data analysis was performed by comparing the sequence of reads with identical UMBs. Base call is determined by the sequence of more than 70% of the UMBs. Only UMBs with more than 2 copies were considered in the data analysis. As shown below, without considering the information from UMB in data analysis, the noise brought by PCR and sequencing error can be as high as 0.24%. If information from UMB is considered in the data analysis, all of the noise can be removed. And the observed frequency of the actual mutant is much closer to the expected frequency of 0.05%.

| Use UMB to distinguish signal from noise | | |
|---|---|---|
| | Without UMB correction (frequency) | After UMB correction (frequency) |
| A* | 99.718% | 99.978% |
| C | 0.024% | 0.000% |
| T | 0.001% | 0.000% |
| G* | 0.254% | 0.032% |
| N | 0.002% | 0.000% |
| D | 0.001% | 0.000% |

*Template DNA obtained by spiking in wild type (A) with PIK3CA H1045KR mutant (G) genomic DNA. 0.05% variant ~10 moleucles (G) frequency was expected.

Figure 6:
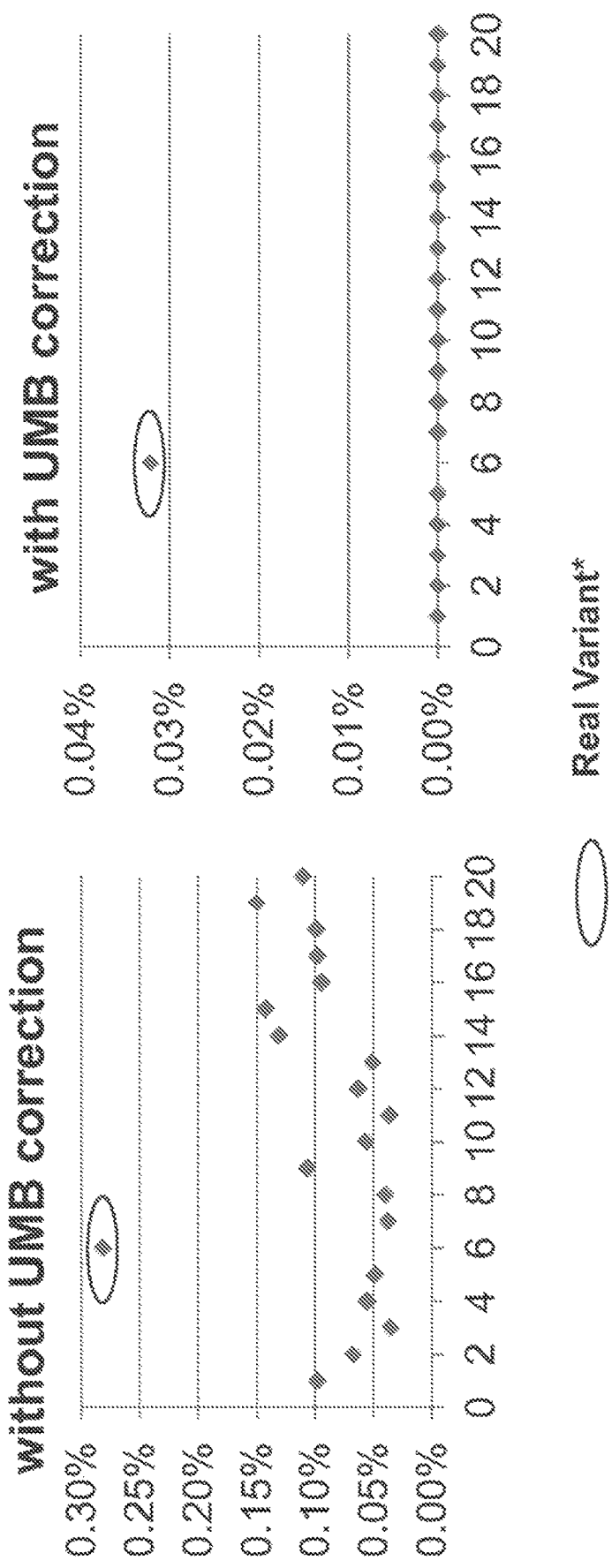
FIG. 6 shows a comparison of nucleotide mismatch rates with (right) and without (left) the use of unique molecular barcode correction.

In this regard, FIG. 6 shows a comparison of nucleotide mismatch rates with (right) and without (left) the use of unique molecular barcode correction. Briefly, the mismatch rate for 20 positions around the expected mutation site was shown with and without considering information from UMB in data analysis. As shown in FIG. 6, without UMB the results were included significant non-specific noise. The noise can be as high as 0.15%. After considering the information from UMB in data analysis, all of the noise was removed.

Throughout this application various publications have been referenced within parentheses. The disclosures of these publications in their entireties, including any GenBank and GI number publications, are hereby incorporated by reference in this application in order to more fully describe the state of the art to which this disclosure pertains.

Although the disclosure has been described with reference to the disclosed embodiments, those skilled in the art will readily appreciate that the specific examples and studies detailed above are only illustrative of the disclosure. It should be understood that various modifications can be made without departing from the spirit of the disclosure. Accordingly, the disclosure is limited only by the following claims.

What is claimed is:

1. A method for determining a true nucleic acid sequence variant, comprising:
   (a) contacting a nucleic acid sample comprising a plurality of target polynucleotides with gene specific forward and reverse primers under conditions sufficient for hybridization, each species of said gene specific forward primer comprising a unique sequence index and an adapter;
   (b) amplifying by polymerase chain reaction (PCR) said plurality of target polynucleotides to produce a plurality of amplicons;
   (c) directly contacting a plurality of target specific capture primers immobilized on a solid support with said plurality of amplicons under conditions sufficient for hybridization to produce a first plurality of immobilized amplicons, said solid support further comprising a plurality of universal capture primers;
   (d) extending said plurality of target specific capture primers to produce a plurality of immobilized extension products complementary to said target polynucleotides, wherein said immobilized extension products comprise a terminal adapter portion capable of hybridizing to said universal capture primers;
   (e) annealing said plurality of universal capture primers to said plurality of said immobilized extension products;
   (f) amplifying by PCR said plurality of immobilized extension products to produce a second plurality of immobilized amplicons, wherein said second plurality of immobilized amplicons comprises a uniformity of 85% or more;
   (g) sequencing said second plurality of immobilized amplicons, and
   (h) eliminating random sequence errors for one or more target polynucleotide by comparing three or more nucleotide sequences at a variant position for a target polynucleotide species, wherein said target polynucleotide species are identified by said unique sequence index to thereby determine a true nucleotide sequence variant in said one or more target polynucleotides.

2. The method of claim 1, wherein said plurality of target polynucleotides comprises 10 ng or less input nucleic acid.

3. The method of claim 1, wherein said conditions sufficient for hybridization comprise incubation for 10 minutes or less.

4. The method of claim 1, wherein a mismatch rate of 0.3% or less for a variant nucleotide position is detected.

5. The method of claim 1, wherein contacting step (a) comprises a first round of PCR amplification with a first gene specific forward and reverse primers and a second round of PCR amplification with a second forward primer complementary to a portion of said first gene specific forward primer, second forward primer comprising said unique sequence index and said adapter.

6. The method of claim 1, wherein said adapter is complementary to said plurality of universal capture primers.

7. The method of claim 1, wherein said amplification of said plurality of target polynucleotides comprises asymmetrical PCR.

8. The method of claim 1, wherein said amplification of said plurality of target polynucleotides comprises multiplex amplification.

9. The method of claim 8, wherein said multiplex amplification comprises a multiplexicity of 180 or more.

10. The method of claim 1, wherein said solid support further comprises a second plurality of universal capture primers.

11. The method of claim 10, wherein said plurality of target specific capture primers further comprise a universal capture primer region.

12. The method of claim 11, wherein said universal capture primer region has a nucleotide sequence corresponding to said second plurality of universal capture primers.

13. The method of claim 1, wherein said plurality of target specific capture primers comprise 200 or more different nucleotide sequences.

14. The method of claim 1, wherein said plurality of target polynucleotides comprise 200 or more different nucleotide sequences.

15. The method of claim 1, wherein said plurality of target polynucleotides comprise a plurality of genomic nucleic acids.

16. The method of claim 1, wherein said amplification of said immobilized extension products comprises bridge amplification.

17. The method of claim 1, wherein said solid support comprises a flow cell.

18. The method of claim 1, wherein said sequencing comprises 50 cycles.

19. The method of claim 18, wherein a start-to-finish time comprises 3 hours or less.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
aatgatacgg cgaccaccga                                           20

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
caagcagaag acggcatacg a                                         21

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
tcggtggtcg ccgtatcatt                                           20

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
tcgtatgccg tcttctgctt g                                         21

<210> SEQ ID NO 5
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (23)..(23)
<223> OTHER INFORMATION: n=uracil
<220> FEATURE:
<221> NAME/KEY: misc_feature
```

```
<222> LOCATION: (23)..(23)
<223> OTHER INFORMATION: n is a, c, g, or t

<400> SEQUENCE: 5
aatgatacgg cgaccaccga ganctacac                                29

<210> SEQ ID NO 6
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (22)..(22)
<223> OTHER INFORMATION: 8-oxo-guanosine

<400> SEQUENCE: 6
caagcagaag acggcatacg agat                                     24

<210> SEQ ID NO 7
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 7
gtgtagatct cggtggtcgc cgtatcatt                                29

<210> SEQ ID NO 8
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 8
atctcgtatg ccgtcttctg cttg                                     24
```